(12) United States Patent
Baum

(10) Patent No.: US 6,872,535 B2
(45) Date of Patent: Mar. 29, 2005

(54) THREE-DIMENSIONAL ARRAY OF SUPPORTS FOR SOLID-PHASE PARALLEL SYNTHESIS AND METHOD OF USE

(75) Inventor: Stephen A. Baum, Tucson, AZ (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 301 days.

(21) Appl. No.: 09/082,038

(22) Filed: May 20, 1998

(65) Prior Publication Data

US 2003/0068644 A1 Apr. 10, 2003

(51) Int. Cl.$^7$ ............................. C12Q 1/00; B01L 11/00

(52) U.S. Cl. .............................. 435/7.1; 435/DIG. 22; 435/DIG. 40; 435/DIG. 43; 435/DIG. 44; 422/134; 227/125

(58) Field of Search .......................... 227/129; 422/101, 422/134; 435/DIG. 22, DIG. 40, DIG. 43, DIG. 44, 7.1

(56) References Cited

U.S. PATENT DOCUMENTS

| | | |
|---|---|---|
| 4,190,647 A | 2/1980 | Goldstein et al. |
| 4,247,646 A | 1/1981 | Berky et al. |
| 4,631,211 A * | 12/1986 | Houghten .................... 428/35 |
| 4,689,405 A | 8/1987 | Frank et al. |
| 4,728,502 A | 3/1988 | Hamill |
| 4,877,659 A | 10/1989 | Vince |
| 5,047,215 A | 9/1991 | Manns |
| 5,058,773 A * | 10/1991 | Brill et al. ................... 227/129 |
| 5,110,556 A * | 5/1992 | Lyman et al. ............... 422/101 |
| 5,202,418 A | 4/1993 | Lebl et al. |
| 5,227,303 A | 7/1993 | Erdman et al. |
| 5,229,172 A | 7/1993 | Cahalan et al. |
| 5,258,454 A | 11/1993 | Berg et al. |
| 5,288,514 A | 2/1994 | Ellman .......................... 427/2 |
| 5,324,483 A | 6/1994 | Cody et al. |
| 5,338,831 A | 8/1994 | Lebl et al. |
| 5,342,585 A | 8/1994 | Lebl et al. |
| 5,344,613 A | 9/1994 | Nokihara et al. |
| 5,376,400 A | 12/1994 | Goldberg et al. |
| 5,395,594 A | 3/1995 | Nokihara et al. |
| 5,422,270 A | 6/1995 | Caspi |
| 5,463,564 A | 10/1995 | Agrafiotis et al. .......... 364/496 |
| 5,504,190 A | 4/1996 | Houghten et al. .......... 530/329 |
| 5,510,240 A | 4/1996 | Lam et al. |
| 5,529,756 A | 6/1996 | Brennan |
| 5,554,536 A | 9/1996 | Rising |
| 5,565,173 A | 10/1996 | DeWitt et al. |
| 5,567,391 A | 10/1996 | DeWitt et al. |
| 5,571,869 A | 11/1996 | Lee et al. |
| 5,582,801 A | 12/1996 | DeWitt et al. |
| 5,585,275 A | 12/1996 | Hudson et al. |
| 5,591,646 A | 1/1997 | Hudson et al. |
| 5,593,642 A | 1/1997 | DeWitt et al. |
| 5,609,826 A | 3/1997 | Cargill et al. ................. 422/99 |
| 5,612,002 A | 3/1997 | Cody et al. |
| 5,620,895 A | 4/1997 | Naqui et al. |
| 5,624,711 A | 4/1997 | Sundberg et al. |
| 5,643,738 A | 7/1997 | Zanzucchi et al. |
| 5,650,489 A | 7/1997 | Lam et al. |
| 5,651,943 A | 7/1997 | Lam et al. |
| 5,677,195 A | 10/1997 | Winkler et al. |
| 5,688,696 A | 11/1997 | Lebl et al. |
| 5,700,655 A | 12/1997 | Croteau et al. |
| 5,702,672 A | 12/1997 | DeWitt et al. |
| 5,712,171 A | 1/1998 | Zambias et al. |
| 5,714,127 A | 2/1998 | DeWitt et al. |
| 5,716,584 A | 2/1998 | Baker et al. ................. 422/131 |
| 5,723,320 A | 3/1998 | Dehlinger |

(Continued)

FOREIGN PATENT DOCUMENTS

| | | |
|---|---|---|
| GB | 2295152 A | 5/1996 |
| WO | WO 94/05394 | 3/1994 |
| WO | WO 98/15825 | 4/1998 |
| WO | WO 98/17382 | 4/1998 |
| WO | WO 98/17383 | 4/1998 |
| WO | WO 98/21584 | 5/1998 |
| WO | WO 98/33586 | 8/1998 |
| WO | WO 98/40159 | 9/1998 |
| WO | WO 99/32219 | 7/1999 |

OTHER PUBLICATIONS

Frank, Strategies and Techniques in Simultaneous Solid Phase Synthesis Based on the Segmentation of Membrane Type Supports, Bio. Med. Chem. Lett., vol. 3, No. 3, p.425–430, 1993.*

(Continued)

*Primary Examiner*—Bennett Celsa
(74) *Attorney, Agent, or Firm*—Synnestvedt & Lecher LLP

(57) ABSTRACT

A three-dimensional (3D) array of solid-phase supports is adapted to provide parallel synthesis of a library of molecules with 3D diversity. Individual locations in the 3D array may be assigned to selected molecules in the library such that molecules may be synthesized at and retrieved from such locations. Also, the supports include aperture walls in stacked plates; the supports may be suspended within stacked plate apertures; the 3D array include discrete supports arranged in columns in one or more wells; the supports include tube inner walls or be suspended in tubes, the tubes being secured in stacked, two-dimensional (2D) frameworks; or the supports include beads contained in porous enclosures having non-porous side walls and being secured in stacked, 2D frameworks. A support transfer device enables transfer of solid-phase supports used in a 3D array. Such apparatus includes: a rack of rods sized to be inserted through supports and a mechanism to prevent supports from coming off the rack; tubes connected to a vacuum manifold to suction supports one Z plane at a time; or a transfer block having recesses to receive one or more support and at least one gate withholding supports from passing through the gate when in a closed position. A method of 3D synthesis includes: a) functionalizing solid-phase supports; b) placing supports in a 3D array; and c) performing parallel synthesis with 3D diversity. At least one unique $R_1$ group member may be assigned to each Z plane.

23 Claims, 15 Drawing Sheets

U.S. PATENT DOCUMENTS

| | | | |
|---|---|---|---|
| 5,736,412 A | | 4/1998 | Zambias et al. |
| 5,741,462 A | | 4/1998 | Nova et al. |
| 5,751,629 A | | 5/1998 | Nova et al. |
| 5,759,779 A | | 6/1998 | Dehlinger |
| 5,763,263 A | | 6/1998 | Dehlinger |
| 5,766,556 A | | 6/1998 | DeWitt et al. |
| 5,770,455 A | | 6/1998 | Cargill et al. |
| 5,792,431 A | * | 8/1998 | Moore et al. ............... 422/134 |
| 5,846,841 A | | 12/1998 | Sepetov et al. |
| 6,083,682 A | | 7/2000 | Campbell et al. .............. 435/4 |
| 6,168,914 B1 | | 1/2001 | Campbell et al. .............. 435/4 |

OTHER PUBLICATIONS

Lam et al., A new Type of Synthetic Peptide Library . . ., Nature, vol. 354, p. 82. 1991.*

Andres et al., 1998, "A novel parallel distributor for dispensing of IRORI™ RF–encoded tags to microkans in 96–well format", Biotech. Bioeng. (Comb. Chem.) 61:93–94.

Bray et al., 1998, "Simultaneous multiple synthesis by the Multipin™ method: techniques for multiple handling, high throughput characterization and reaction optimization on solid phase",.

Casebier et al., 1998, "Advances in parallel combinatorial synthesis of mapping Arraystm", $216^{th}$ ACS National Meeting, Boston (Abst. 024).

Fodor et al., 1991, "Light–directed, spatially addressable parallel chemical synthesis", Macromolecular Chem. 2:401–405.

Frank, 1993, "Spot synthesis: positionally addressable, parallel chemical synthesis on membrane supports", Proc. Eur. Peptide Symp., $22^{nd}$, pp. 59–60.

Frank and Guler, 1992, "Spot–synthesis: a novel technique for facile and rapid peptide screening", Proc. Am. Pept. Symp., $12^{th}$, pp. 519–520.

Furka, 1988, "More peptides by less labour", Xth Int. Symp. Med. Chem., Hungary (Abst. 288).

Gani et al., 1997, "Permutational organic synthesis in addressable microreactors (POSAM™): an efficient, inexpensive and versatile solid–phase protocol for the preparation of libraries of compounds on the 0.01 to 1.0 millimole (or larger) scale", Tetrahedron Lett. 38:8577–8580.

Krchnak and Lebl, 1995, "Synthetic library techniques: subjective (biased and generic) thoughts and views", Mol. Diversity 1:193–216.

Lam et al., 1997, "The "one–bead–one–compound"combinatorial library method", Che. Rev. 97:411–448.

Merrifield, "Technical service and development department of the Dow Chemical Co.", 85:2152–2154.

Pavia et al., 1997, "Identifying novel leads using combinatorial libraries: issues and successes", Chimia 51:826–831.

Steele, 1997, "Parallel synthesis methodologies for mixtures and single compounds", $2^{nd}$ Ann. Solid–Phase Synthesis Conference., Cambridge.

Swaze et al., 1998, "Automated parallel synthesis of trisubstituted pyrrolidine and piperidine based combinatorial libraries", $215^{th}$ ACS National Meeting, Dallas, Mar. 29–Apr. 2.

Terret et al., 1997, "Drug discovery by combinatorial chemistry—the development of a novel method for the rapid synthesis of single compounds", Chem. Eur. J. 3:1917–1920.

Xiang et al., 1995, "A combinatorial approach to materials discovery", Science 268:1738–1740.

* cited by examiner

THREE-DIMENSIONAL ARRAY OF SUPPORTS FOR SOLID-PHASE PARALLEL SYNTHESIS AND METHOD OF USE

BACKGROUND OF THE INVENTION

1. Technical Field

This invention relates to the field of combinatorial chemistry. More specifically, the invention relates to a three-dimensional (3D) array of supports for solid-phase parallel synthesis and its method of use.

2. Background Art

In recent years the field of combinatorial chemistry has become increasingly important due to the rapidly growing number of potential drug targets emerging from molecular biology research. In past decades, the synthesis of organic chemicals in the pharmaceutical industry was slow and costly. Combinatorial chemistry offers a set of techniques for creating a multiplicity of compounds that may then be screened for bioactivity.

In one use of combinatorial chemistry, large libraries of molecules are produced in parallel while attached to solid-phase supports. A 96-well plate is common tool used in solid-phase parallel synthesis of molecules. Essentially, the 96-well plate is an array of wells having eight rows of twelve wells, wherein each well may be identified by its unique location in the array. A predetermined amount of a solid support material, often resin beads about 20 $\mu$m to 500 $\mu$m in diameter, is placed in each well. The solid support is functionalized prior to placement in the wells such that an initial building block of the molecule to be synthesized on the support will bond with the support. Typical resin beads are manufactured by copolymerizing styrene and divinylbenzene monomers, although other monomers may be used, to produce the beads. As taught in the art, other solid supports may be used, including controlled pore glass, polyacrylamides, poly(ethylene glycol), poly(ethylene glycol)-monomethyl ether, silica gel, cellulose, acrylic acid grafted polypropylene, acid grafted polyethylene, and still other materials. Various functionalities may be chemically joined, typically by covalent bonding, to the resins, such as carboxylic acid, alcohol, halomethyl, chloromethyl (Merrifield), amino, and aminomethyl functionalities. Initial building blocks are then chemically joined to the functionalities and additional building blocks are added sequentially, synthesizing molecules one building block at a time on the support. The addition of building blocks may be designed such that a different series of building blocks is added to each well in the 96-well plate. Thus, the series of reactions that build the molecules on the solid support will yield a different molecule in each well. Accordingly, for a 96-well plate, 96 unique molecules may be synthesized in parallel.

Once synthesized, the molecules may be cleaved from the solid support or left attached, screened for bioactivity, stored in a library of molecules, etc. Many apparatus and methods have been developed for increasing the rapidity with which molecules may be synthesized, cleaved, screened and stored. Examples of some of the apparatus and methods are described in the following patents: Zambias et al., U.S. Pat. No. 5,712,171; Hudson et al., U.S. Pat. Nos. 5,591,646 and 5,585,275; Baker et al., U.S. Pat. No. 5,716,584; DeWitt et al., U.S. Pat. No. 5,714,127; Winkler et al., U.S. Pat. No. 5,677,195; Lam et al., U.S. Pat. No. 5,651,943; Zanzucchi et al., U.S. Pat. No. 5,643,738; Sundberg et al., U.S. Pat. No. 5,624,711; Cargill et al., U.S. Pat. No. 5,609,826; Lee et al., U.S. Pat. No. 5,571,869; Brennan, U.S. Pat. No. 5,529,756; Nokihara et al., U.S. Pat. No. 5,395,594; Goldberg et al., U.S. Pat. No. 5,376,400; Berg et al., U.S. Pat. No. 5,258,454; Cahalan et al., U.S. Pat. No. 5,229,172; Frank et al., U.S. Pat. No. 4,689,405; Hamill, U.S. Pat. No. 4,728,502; and Houghten, U.S. Pat. No. 4,631,211, each of which is herein incorporated by reference for its pertinent and supportive teachings.

In each of the above patents, the number of molecules that may be synthesized is typically limited by the number of available wells. It is possible to place a mixture of supports having different initial building blocks in one well and thus synthesize multiple molecules in one well. However, it is difficult and costly using current technology to later segregate the molecules when needed. Accordingly, plates have been fabricated having more rows and columns of wells than the typical 96-well plate. For example, a 384-well plate is also common. Generally, the number of wells is increased by decreasing the size of individual wells such that more wells will fit within the size limitations of a well plate. However, if the wells are smaller, then less support material may be placed in a given well and, in turn, a lesser amount of a molecule may be synthesized in the well.

Often, portions of the synthesis process are conducted with automated devices that distribute among the wells the correct amount and type of reagents needed to add building blocks. One size limitation of a well plate is the maximum dimension that an existing automated device will accept. Other size limitations may exist depending upon other equipment used in the synthesis process that has been fabricated to accommodate a particular size of well plate. Also, the size of individual wells may be limited by equipment constraints. It is conceivable that an individual well could become too small to be compatible with the devices used to distribute reagents, insert and retrieve solid supports, etc. Wells that are too small could introduce errors into the synthesis process if reagents and supports cannot be accurately delivered to and retrieved from the wells. In addition, the automated devices and other equipment are often quite costly and changing to a new well plate, even though improved, may require the replacement of equipment designed to accommodate the new well plate. Therefore, there existed a need to increase the number of molecules that may be accurately synthesized in a well plate without the expense of replacing automated devices or other equipment.

After synthesis, molecules are screened and then stored, since a need may arise to conduct further screening or testing of a given batch of molecules. The stored molecules are referred to as a library of molecules. A library can take many forms, but often comprises a collection of small vials, capped well plates, or similar storage containers, each vial or well containing a solution with a single type of molecule that was synthesized in a well plate and, often, cleaved from a solid support. The collection of vials, well plates, etc. can be difficult to manage, since combinatorial chemistry technology is capable of yielding an immense number of unique molecules. That capability translates into an equally immense number of vials, wells, etc. Accordingly, there also existed a need to improve the method of forming libraries and provide less awkward management thereof.

Thus, it can be seen from the above discussion that it would be an improvement in the art to provide a technology and tools that increase the number of molecules that may be accurately synthesized using existing and new equipment and to provide an improved method of creating a library of the molecules synthesized.

DISCLOSURE OF INVENTION

According to the present invention, an apparatus is provided that includes a three-dimensional (3D) array of solid-phase supports, the array adapted to provide parallel synthesis of a library of molecules with 3D diversity. By way of example, one such apparatus allows individual locations in the 3D array to be assigned to selected molecules in the library such that selected molecules may be synthesized at and retrieved from their respective locations. Other examples of apparatus include those wherein: 1) the supports include the walls of apertures formed in plates; 2) the supports are suspended within apertures formed in plates; 3) the 3D array includes a plurality of discrete supports arranged in a plurality of columns in one or more wells; 4) the supports include the inner walls of tubes or the supports are suspended in tubes, the tubes being secured in two-dimensional (2D) frameworks, wherein the 3D array includes a plurality of such 2D frameworks of tubes stacked with the inner walls of the tubes substantially aligned, and wherein the inner walls form side walls for a plurality of wells; or 5) the supports comprise beads contained in porous enclosures, the porous enclosures having non-porous side walls and being secured in 2D frameworks, wherein the 3D array comprises a plurality of such 2D frameworks of porous enclosures stacked with the enclosure side walls substantially aligned, and wherein the enclosure side walls form side walls for a plurality of wells.

An apparatus is also provided including a support transfer device adapted to enable transfer of solid-phase supports used in a 3D array of solid-phase supports, the array adapted to provide parallel synthesis of a library of molecules with 3D diversity. One example of such an apparatus includes a plurality of rods sized to be inserted through an aperture formed in each support and a mechanism to prevent the supports from coming off the rack. Another example includes a plurality of tubes connected at a first end of the tubes to a manifold, the tubes being adapted each to suction at a second end of the tube one support taken from each column of supports in the 3D array when a vacuum is applied to the manifold. Yet another example includes a transfer block having a plurality of recesses, the recesses being sized to receive one or more support and being spaced to substantially align with at least a portion of a plurality of wells of the 3D array, and at least one gate slidably engaged with the transfer block, each gate having apertures formed therein, wherein sliding the gate into an open position allows one or more supports to pass through apertures in the gate and sliding the gate into a closed position withholds supports from passing through the gate.

According to the present invention, a method is also provided including the steps of: a) functionalizing a plurality of solid-phase supports; b) placing the plurality of supports in a 3D array; and c) performing parallel synthesis of a library of molecules in the 3D array of supports with 3D diversity. In one example of such a method, a step of attaching a $R_1$ group member (initial building block) to each support is performed before the step of placing the plurality of supports in the 3D array. Also, in another example, the supports in the 3D array are arranged in a plurality of planes stacked in a Z direction and the step of placing the plurality of supports in the 3D array includes assigning at least one unique $R_1$ group member to each plane.

The foregoing and other features and advantages of the present invention will be apparent from the following more particular description of preferred embodiments of the invention, as illustrated in the accompanying drawings.

BRIEF DESCRIPTION OF DRAWINGS

Preferred embodiments of the present invention will hereinafter be described in conjunction with the appended drawings, where like designations denote like elements, and.

BEST MODE FOR CARRYING OUT THE INVENTION

Figure 1:
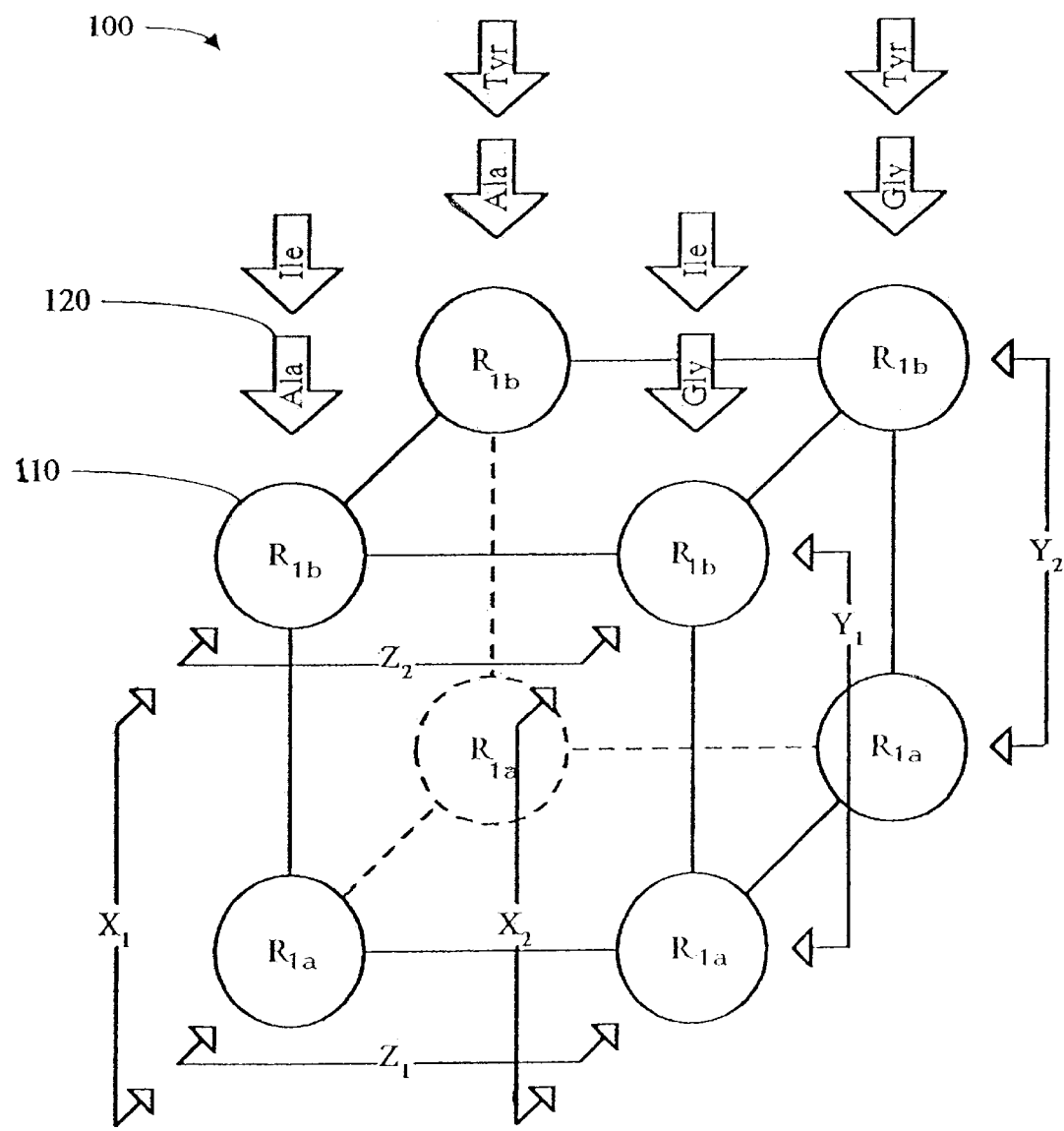
FIG. 1 is a diagram showing the concept of three-dimensional (3D) parallel synthesis according to the present invention.

A preferred embodiment of the present invention provides an apparatus that includes a three-dimensional (3D) array of solid-phase supports with the array adapted to provide parallel synthesis of a library of molecules with 3D diversity. Such molecules include peptides, oligonucleotides, and general organic compounds, but are not limited to those. Also, the terms "solid-phase support," "solid support," and "support" include any material that may be functionalized and is compatible for use in combinatorial chemistry, as known in the art and/or described herein. Essentially, multiple supports arranged in multiple columns form the 3D array in such a way to allow addition of a unique sequence of building blocks to each column of supports. If a unique initial building block is first added to each support in a given column, then the addition of the same sequence of building blocks to each support in the column will yield a unique molecule on each support in the column. Since the molecules on each support in a given column may be unique and unique sequences may be added to each column, it is possible for each support in the 3D array to possess a unique type of molecule with respect to all other supports in the 3D array. Also, although it may be preferred in some circumstances as discussed below, it is not required in the present invention for each initial building block on the supports of a given column to be unique or for a unique sequence of building blocks to be added to each column of supports. Rather, it is possible to obtain 3D diversity, as defined below, with some repetition of initial building blocks or sequences of building blocks.

In a preferred embodiment, individual locations in the 3D array may be assigned to selected molecules in the library such that selected molecules may be synthesized at and retrieved from their respective locations. In other preferred embodiments: 1) the supports include the walls of apertures formed in stacked plates; 2) the supports are suspended within apertures formed in stacked plates; 3) the 3D array includes a plurality of discrete supports stacked in a plurality of columns in one or more wells; 4) the supports include the inner walls of tubes, or the supports are suspended in tubes, that are secured in stacked, two-dimensional (2D) frameworks, wherein the inner walls of tubes form side walls for a plurality of wells; or 5) the supports include beads contained in porous enclosures having non-porous side walls and being secured in stacked, 2D frameworks, wherein the enclosure side walls form side walls for a plurality of wells.

A preferred embodiment of the present invention also includes a support transfer device adapted to enable transfer of solid-phase supports used in a 3D array of solid-phase supports. One preferred embodiment of such an apparatus includes a plurality of rods sized to be inserted through an aperture formed in each support and a mechanism to prevent the supports from coming off the rack. Another preferred embodiment includes a plurality of tubes connected at a first end of the tubes to a manifold, the tubes being adapted each to suction at a second end of the tube one support taken from each column of supports in the 3D array when a vacuum is applied to the manifold. Yet another preferred embodiment includes a transfer block having a plurality of recesses sized to receive one or more support and at least one gate slidably engaged with the transfer block, each gate having apertures formed therein, wherein opening the gate allows one or more supports to pass through the apertures and closing the gate withholds supports from passing through the gate.

According to another preferred embodiment, a method is also provided including the steps of: a) functionalizing a plurality of solid-phase supports; b) placing the plurality of supports in a three-dimensional (3D) array; and c) performing parallel synthesis of a library of molecules in the 3D array of supports with 3D diversity. In one preferred embodiment of such a method, the supports in the 3D array are arranged in a plurality of planes stacked in a Z direction and the step of placing the plurality of supports in the 3D array includes assigning at least one unique $R_1$ group member to each plane.

FIG. 1 shows a three-dimensional (3D) array 100 including eight solid-phase supports 110 positioned relative to one another such that they may be considered to represent the eight corners of a cube. The FIG. 1 diagram is instructive in explaining the concept of 3D parallel synthesis according to the present invention, but the various mechanisms for actually performing parallel synthesis of a library of molecules in a 3D array of solid supports are described below. Essentially, solid-phase supports are first functionalized, according to methods known in the art, such that a first building block of a molecule to be synthesized on the solid-phase supports will chemically join with the supports. Chemical joining is preferably covalent bonding, but may also include other bonding such as ionic bonding, coordinate-covalent linkage, chelation, etc.

Various functionalization techniques may be used in the present invention. For example, graft polymerization of polymer solid supports is one example of such functionalization techniques as described in U.S. Pat. No. 5,571,869, U.S. Pat. No. 5,376,400, and U.S. Pat. No. 5,229,172. Thus, graft polymerization of a polymer solid support may occur by grafting a monomer, such as styrene, by a radical initiated process such as exposure of a substrate and monomer to gamma or UV irradiation, a plasma, or an electron beam. Instead of grafting a monomer to the support along with successively adding monomers to build a grafted polymer, an existing polymer may be grafted to the support. Also, such monomers and polymers may already include a functionality or the grafted polymer may be functionalized after grafting is complete. Alternatively, a polymer solid support may be directly functionalized using techniques such as surface modification by plasma deposition or by chemical surface modification. In direct functionalization, a functionality is chemically joined to the polymer solid support without first grafting a polymer to support the functionality. Functionalizing solid supports other than polymer solid supports, such as glass, is also possible and one example is described in U.S. Pat. No. 5,624,711. Once a solid support is functionalized, a linking compound may be chemically joined to the grafted polymer if desired. Whether or not a linking compound is added, a first building block, such as an amino acid, nucleotide, organic compound or other compound, may then be chemically joined to the solid-phase support by joining the first building block either to the functionality or the linking compound. Additional building blocks may be added to the first building block, thus synthesizing a desired molecule on the solid support. Once synthesized, the molecule may be stored on the support or cleaved from the linking compound and used in subsequent testing. The first building block is denoted in FIG. 1 as $R_1$, representing a group of building blocks that may be selected for the first building block. Accordingly, $R_{1a}$ denotes selection of building block "a" for the first building block and $R_{1b}$ denotes selection of building block "b" for the first building block, wherein each building block is a chemical compound.

Array 100 of supports 110 may be described as having X, Y and Z planes as denoted in FIG. 1. The $X_1$ plane, as designated in FIG. 1, is a vertical plane and includes the two columns of supports 110 representing the four corners of the left face of the cube shown in FIG. 1. The bottom support in each of the two columns has "a" for its $R_1$ building block while the top support in each of the two columns has "b" for its $R_1$ building block. Accordingly, each support 100 placed in a given column has a unique $R_1$ building block, the first building block. Plane $X_2$ is defined similarly, except that it includes the two columns of supports 110 representing the four corners of the right face of the cube shown in FIG. 1. In turn, plane $Y_1$ includes the two columns of supports 110 at the front face of the cube and plane $Y_2$ includes the two columns of supports 110 at the back face of the cube. Planes $Z_1$ and $Z_2$, however, are different from the X and Y planes in that they are horizontal planes. Plane $Z_1$ includes the tier of four supports 110 representing the four corners of the bottom face of the cube shown in FIG. 1. Since the bottom supports 110 in each of the columns defining the X and Y planes has "a" for their $R_1$ building block, all supports 110 in plane $Z_1$ also have "a" for their $R_1$ building block. Plane $Z_2$ is defined similarly, except that it includes the tier of supports 110 represent the top face of the cube, each support having "b" for its $R_1$ building block.

The advantage of performing parallel synthesis of a library of molecules on a 3D array of solid-phase supports is to generate 3D diversity, that is to synthesize different molecules on the various supports 110 in 3D array 100. When complete 3D diversity exists, every location in 3D array 100 (the corners of the cube) contains a unique molecule with respect to every other location. The present invention is best used to achieve complete 3D diversity among the locations in 3D array 100 or some other 3D array of solid supports. However, the scope of the present invention also includes partial 3D diversity, wherein at least one location, but not every location, in a 3D array contains a unique molecule with respect to every other location. Accordingly, unless indicated otherwise, the term "3D diversity" as used herein and in the claims below refers both to complete 3D diversity and to partial 3D diversity. Partial 3D diversity is generally not preferred in a 3D library of molecules unless replicate synthesis of selected molecules is desired. Current technology does not even provide a 3D array of solid supports, much less 3D diversity. Rather, current art only provides two-dimensional (2D) diversity, which may be contrasted with partial 3D diversity. In a 2D array, it is not possible to have 3D diversity. However, it is possible to have only 2D diversity in 3D array. Even though each molecule in the locations of a given plane is unique from the molecules of every other location in the same plane, only 2D diversity exists if the molecule of every location in each plane is repeated at least once in another plane. In other words, every plane of a 3D array may possess complete diversity only as to the locations with a given plane, but if the molecule of every location in each plane is repeated at least once in another plane, then only 2D diversity has been achieved.

FIG. 1 displays one circumstance among many possible circumstances wherein complete 3D diversity may be obtained according to a preferred embodiment of the present invention. In this example, several amino acids are used as building blocks, however, they are used by way of example only and many other compounds may alternatively be used as previously indicated. First, it should be noted that each Z plane includes supports having unique $R_1$ building blocks with respect to all supports in the other Z plane. That is, plane $Z_1$ supports include only $R_{1a}$ and plane $Z_2$ supports include only $R_{1b}$. Next, a third unique building block, alanine (Ala), is added as the $R_2$ building block to the supports in plane $X_1$ and a fourth unique building block, glycine (Gly), is added as the $R_2$ building block to the supports in plane $X_2$. Accordingly, the $R_2$ group includes Ala and Gly. Finally, a fifth unique building block, isoleucine (Ile), is added as the $R_3$ building block to the supports in plane $Y_1$ and a sixth unique building block, tyrosine (Tyr), is added as the $R_3$ building block to the supports in plane $Y_2$. Accordingly, the $R_3$ group includes Ile and Tyr. The result of the above process is that eight unique molecules are synthesized in parallel, one unique molecule on each support 110. The eight molecules are Ile-Ala-$R_{1a}$, Tyr-Ala-$R_{1a}$, Ile-Gly-$R_{1a}$, Tyr-Gly-$R_{1a}$, Ile-Ala-$R_{1b}$, Tyr-Ala-$R_{1b}$, Ile-Gly-$R_{1b}$, and Tyr-Gly-$R_{1b}$, wherein each $R_1$ building block is joined to a solid support 110. Three building blocks are added to each of the eight solid-phase supports 110 in 3D array 100 of FIG. 1, wherein each building block is selected from a R group of two possible building blocks. Since there are two possible building blocks in each R group and three R groups are used, $2^3$ (=8) possible combinations exist for adding the R groups in the order indicated, and each of the possible combinations is synthesized in 3D array 100 shown in FIG. 1.

To synthesize a unique molecule at each location in 3D array 100, under the circumstances indicated, it is required that all supports in each Z plane include unique $R_1$ building blocks with respect to all supports in the other Z plane. Since the same $R_2$ and $R_3$ building blocks are added to both supports in each column, the same molecule would be synthesized on any supports in the same column were it not for the different $R_1$ building block. For example, if all the supports in plane $Z_2$ included $R_{1a}$, then only four unique building blocks would be synthesized and only 2D diversity would be obtained. That is, each molecule in plane $Z_1$ would be unique from every other molecule in plane $Z_1$, but every molecule in plane $Z_1$ would be repeated in the location above it in plane $Z_2$.

Understandably the process described may be varied in several ways and still yield 3D diversity in 3D array 100. For example, the R groups may include common building blocks and still produce 3D diversity. If $R_3$ included Ile and Gly, instead of Ile and Tyr, then the eight moleculess synthesized would be $R_{1a}$-Ala-Ile, $R_{1a}$-Ala-Gly, $R_{1a}$-Gly-Ile, $R_{1a}$-Gly-Gly, $R_{1b}$-Ala-Ile, $R_{1b}$-Ala-Gly, $R_{1b}$-Gly-Ile, and $R_{1b}$-Gly-Gly. That is, even though the discussion above provided six unique building blocks for the building blocks, they were not required to produce 3D diversity. As common building blocks are used among different R groups, it becomes more likely that some combinations will be repeated. However, such repetition may be predicted by computing the combinations that will be produced under the planned circumstances and comparing the combinations for repeat molecules. The computation may be performed using a computer program so designed.

Another variation is including three or more building blocks in the $R_1$ group such that the supports in either Z plane include more than one variety of $R_1$ building block. While it is possible that such action might prevent 3D diversity, it is equally possible that 3D diversity may be maintained with proper location selection for the $R_1$ building blocks. If three or more building blocks are used for the $R_1$ group, however, then not every possible combination will be generated in 3D array 100 since only eight locations exist and more than eight possible combinations would exist. Similarly, if four or more R groups are added to each support 110, then not every possible combination will be synthesized, since there are more than eight possible. In some applications in may not be important to synthesize every possible combination, or it may even be desirable to synthesize repetitive molecules at certain locations in 3D array 100.

Figure 2:
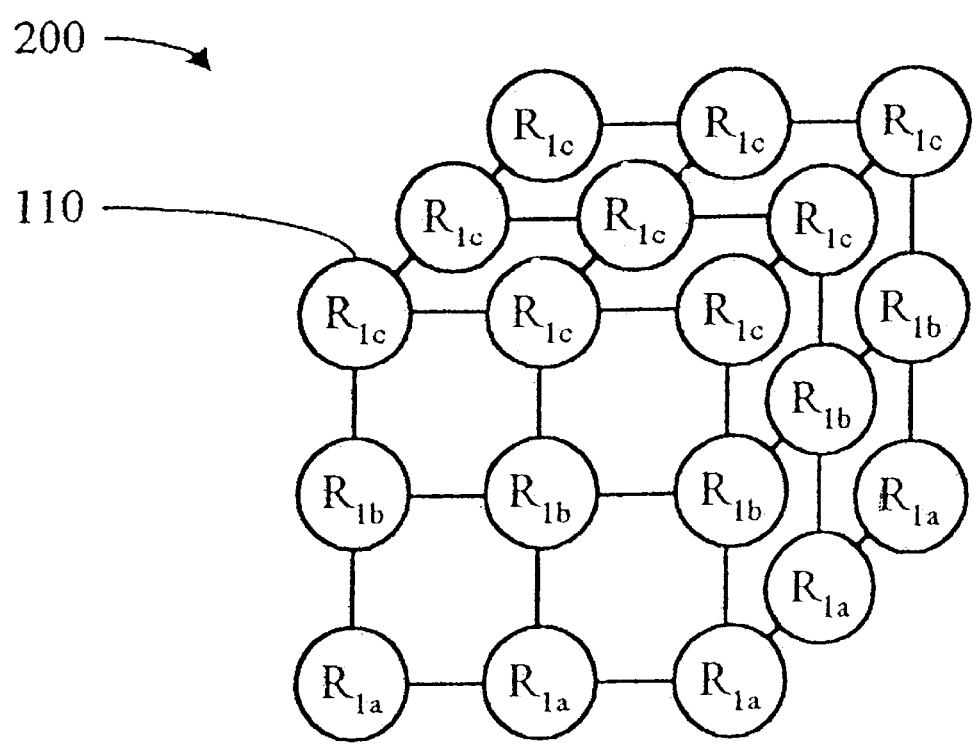
FIG. 2 is a diagram further showing the concept of 3D parallel synthesis according to the present invention.

The concepts described above and in FIG. 1 may be expanded to provide synthesis of a very large number of unique molecules in a 3D array of solid-phase supports with 3D diversity as shown in FIG. 2. FIG. 2 expands the concept of FIG. 1 by adding supports 110 to create one new X, Y, and Z plane of supports 110. Accordingly, a total of 27 solid-phase supports 110 exist in 3D array 200 of FIG. 2. For a molecule wherein three building blocks are in each R group, three R groups are used, and all nine building blocks are unique, a total of $3^3$ (=27) combinations are possible when adding the R groups in only one order and not repeating any building blocks in the sequence. Each of the 27 possible combinations may be synthesized in 3D array 200 shown in FIG. 2. Conceivably, 3D array 200 of FIG. 2 displays how additional X, Y, and/or Z planes of supports 110 may be added to provide synthesis of a very large number of molecules. For example, a 3D array of eight X planes, twelve Y planes, and ten Z planes will possess a total of 960 solid support locations for synthesis of 960 unique molecules. Such a 3D array may be compared to a standard 96-well plate, wherein typically only 96 molecules may be synthesized, one for each well.

In current technology, the number of molecules that may be synthesized is typically limited by the number of available wells in the well plate. It is possible to place a mixture of supports having different $R_1$ building blocks in each well and thus synthesize multiple different molecules in each well. However, it is difficult and costly using current technology to later segregate the supports and molecules when needed. Accordingly, a preferred embodiment of the present invention provides a mechanism for assigning individual locations in a 3D array to selected molecules. The selected molecules may then be synthesized at and retrieved from the assigned locations when desired. That is, rather than a simple mixture of supports with different molecules synthesized thereon, a preferred embodiment provides synthesis in an orderly array, wherein the location of individual molecules is known and may be used to retrieve a selected molecule. In addition, the present invention provides an apparatus wherein a large number of molecules may be generated under the identical process conditions without as much concern over batch to batch variations. In current technology, a larger number of well plates are required so more opportunity for batch to batch variations exist.

Described below are several embodiments and variations on embodiments that provide the benefits described above. The embodiments below are provided as examples of implementing the principles above for parallel synthesis of a library of molecules on a 3D array of solid-phase supports. Various changes in form and details may be made without departing from the principles described and the scope of the invention.

Figure 3:
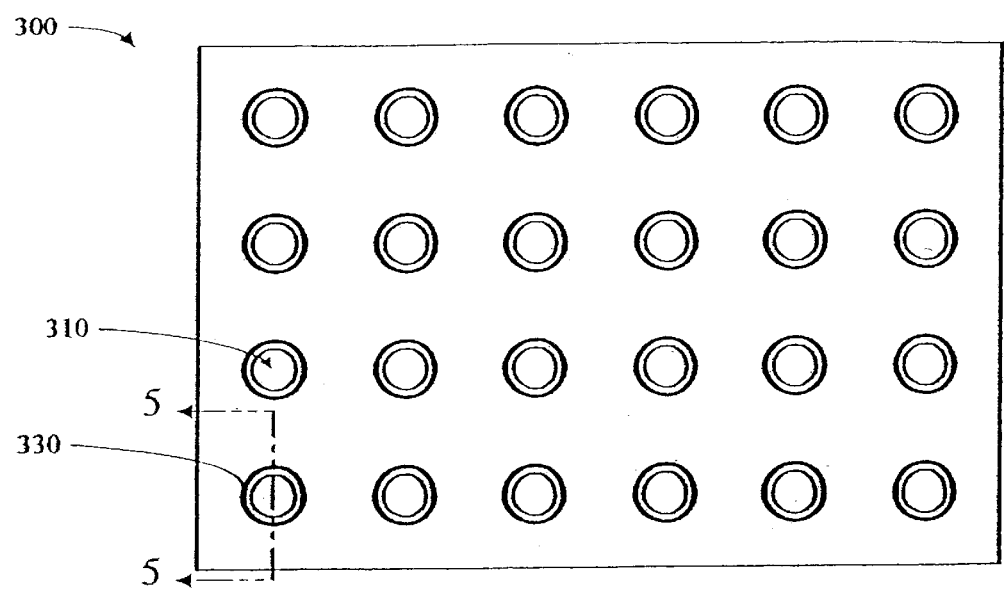
FIG. 3 is a top view of a plate providing a solid support for 3D parallel synthesis.

According to a preferred embodiment of the present invention, parallel synthesis of a library of molecules with 3D diversity may be carried out in stacked plates, wherein the supports include either the walls of apertures formed in the plates, supports suspended within apertures formed in the plates, or both. FIG. 3 shows one example of the preferred embodiment in a top view of a stackable plate 300 adapted to provide solid-phase supports and reagent wells for synthesizing molecules in parallel with 3D diversity. Plate 300 includes a four by six 2D array of apertures 310, each with an O-ring 330. The number of apertures in plate 300 may be modified as needed. For example, plate 300 may provide 96 apertures that are spaced to accommodate equipment typically used in combinatorial chemistry, such as equipment adapted for use with 96-well plates and other plates with a different number of wells. Apertures 310 formed through plate 300 shown in FIG. 3 are circular and the walls of apertures 310 provide a surface that may be functionalized and used as a solid-phase support. Accordingly, plate 300 could be fabricated from several different materials and apertures 310 could be many other shapes, including shapes designed to provide aperture walls with a greater surface area than possible with a circular aperture of comparable size. For example, a star-shaped aperture is one possibility. In general, plate 300 could be fabricated from any type of glass, plastic, or other material that may be functionalized to provide a solid-phase support and that meets the standards and criteria needed for apparatus used in combinatorial chemistry as determined by those skilled in the art. Exemplary materials include pharmaceutical grade glass, silica gel, alumina gel, cellulose, polyolefins, polypropylene, polyethylene, halogenated polyolefins, TEFLON (polytetrafluoroethylene available from E.I. Du Pont de Nemours and Co. in Wilmington, Del.), poly(chlorotriflouroethylene), polyamides, polyimides, poly (paraxylylenes), phenol-formaldehyde polymers, resin coated on or adhered to the listed materials and other structurally supportive materials, combinations of the listed materials, etc.

Figure 4:
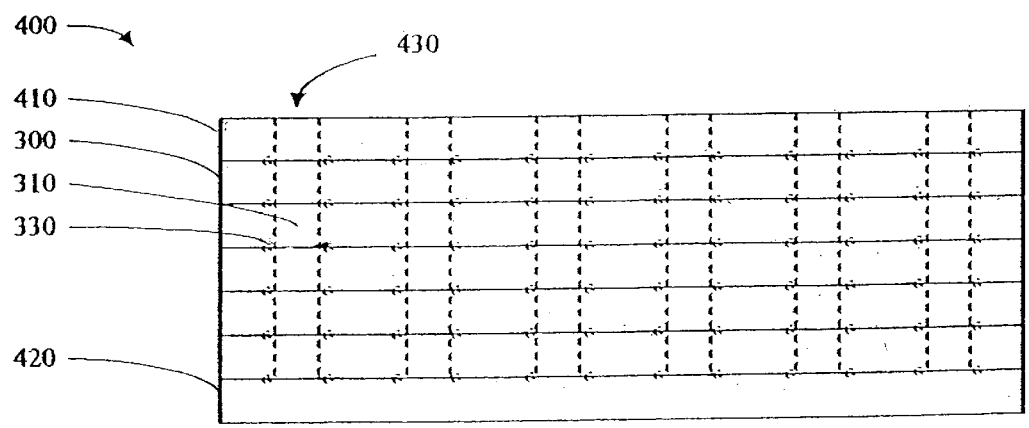
FIG. 4 is a side view of stacked plates forming a 3D array of solid supports.

FIG. 4 shows a 3D array 400 of solid-phase supports formed by stacking five identical plates 300 on end plate 420 along with optional top plate 410. By substantially aligning apertures 310 of each plate 300, the aperture walls form side walls for wells 430. End plate 420 includes O-rings 330 as does each plate 300 to prevent cross contamination, that is, undesirable transfer of reagents, building blocks, etc. from one well to another. For example, if O-rings 330 or some other sealing mechanism for preventing cross contamination were not provided, then the molecules synthesized on the walls of apertures 310 could become contaminated. That is, the incorrect molecules could be synthesized due to the incorrect reagent leaking between plates 300 to neighboring wells 430. Optional top plate 410 similarly prevents cross contamination by acting as a sort of splash guard to prevent splashing or spilling of reagents from one well 430 to another. Top plate 410 preferably need not include O-rings 330 and is preferably not functionalized since it acts primarily to prevent cross contamination, rather than to provide a solid-phase support. Although not shown, draining orifices may also be formed through end plate 420 such that application of a vacuum to the orifices quickly drains reagents from each well 430. Such orifices are highly desirable if 3D array 400 is to be used in an automated synthesis device for delivering reagents. Although not preferred, end plate 420 could also be left out of 3D array 400 such that plate 300 on the bottom functioned as end plate 420 with apertures 310 functioning as draining orifices.

Figure 5:
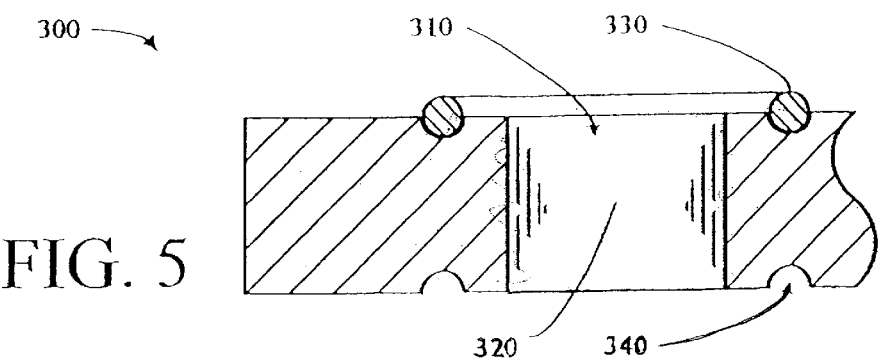
FIG. 5 is a cross-sectional view of the plate in FIG. 3 taken along line 5—5.

FIG. 5 shows a cross sectional view of one aperture 310 and a portion of plate 300 taken along line 5—5 as shown in FIG. 3. FIG. 5 thus displays a portion of plate 300 with aperture 310, solid-phase support 320 (the walls of aperture 310), O-ring 330, and O-ring seat 340. O-ring 330 and O-ring seat 340 provide an example of one sealing mechanism for preventing cross contamination between wells 430. Other exemplary sealing mechanisms are shown in FIGS. 6, 7, 9, 10 and 21 and are discussed below. Even though the sealing mechanisms of FIGS. 6, 7, 9, 10 and 21 are associated with the various solid supports shown therein, the sealing mechanisms may be interchanged among any of the various solid supports used in the stacking plate embodiment of FIGS. 3–11. In addition, each of the sealing mechanisms and various solid supports used in the stacking plate embodiment of FIGS. 3–11 may be incorporated into the stacking tube framework embodiment from the discussion below regarding FIGS. 21 and 22.

Three dimensional array 400 of solid-phase supports 320 is used by first functionalizing at least supports 320 (the walls of apertures 310). Other portions of plate 300 might be functionalized during the functionalizing process, since it may be easier to functionalize one entire plate 300 at a time rather than to target only apertures 310. Next, $R_1$ groups are added at least to supports 320, wherein each plate 300 may be considered one Z plane of supports as discussed above with regard to FIGS. 1 and 2. Once each support 320 includes an $R_1$ group, plates 300 are stacked in combination with end plate 420 and optional top plate 410 to form 3D array 400 and multiple wells 430. Reagents are then applied to synthesize the desired molecule at each location in 3D array 400, wherein each aperture 310 through a single plate is one location. Once the molecules are synthesized, the plates may be stored separately or together, used in the additional of more building blocks on the molecules already synthesized, and/or prepared for cleavage of the molecules from supports 320. For example, plates 300 from one 3D array 400 may be separated and combined with one or more plates 300 from one or more other 3D arrays 400 to further diversify the molecules already formed thereon by adding yet more building blocks.

Figure 6:
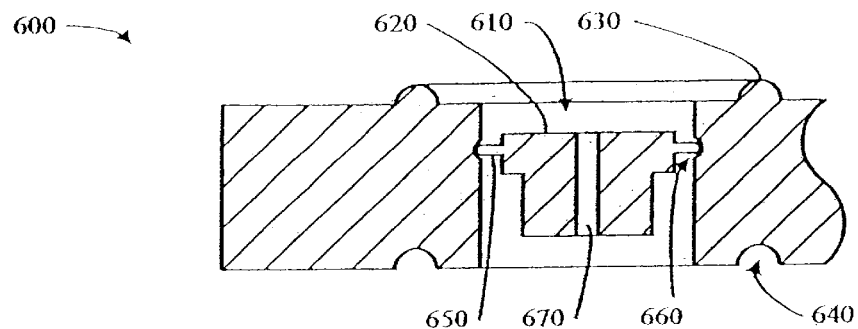
FIG. 6 is a cross-sectional view a tube support suspended in a plate aperture.

FIG. 6 displays a cross-section view similar to that shown in FIG. 5 except that stackable plate 600 is shown with solid-phase support 620 temporarily suspended in aperture 610 formed through plate 600. As with plate 300 discussed above, disk support 620 could be fabricated from a wide variety of materials, including those previously listed. Essentially, support 620 is a disk with spokes 650 extending from the periphery of the disk such that they align with recess 660 formed in the walls of aperture 610. Such a disk support 620 may be snapped into position in plate 600 after disk support 620 is functionalized and may be snapped out of position for cleavage of a synthesized molecule or storage. Alternatively, disk support 620 and the walls of aperture 610 may be functionalized together after disk support 620 is snapped into place. Spokes 650 may also be affixed to the walls of aperture 610 or formed integrally to plate 600 from the same material. For example, plate 600, spokes 650, and disk support 620 could be formed in the same mold. If affixed or formed integrally, then disk support 620 probably must be cut from plate 600 to remove it, if desired.

The gap shown in FIG. 6 that is bridged by spokes 650 allows the passage of reagents around disk support 620, through aperture 610, and on to other apertures 610 in other plates 600. Orifice 670 through disk support 620 similarly encourages flow of reagents through aperture 610 and also provides a opening for inserting a rod (not shown) as when it is desired to form an orderly stack of disk supports 620 not positioned in plate 600. The shape of disk support 610 shown in FIG. 6 may be modified to address other considerations. For example, it may be that disk support 620 has multiple perforations formed through it such that greater surface area is provided or is shaped to accommodate easy flow of relatively viscous liquids around disk support 620 and through aperture 610 or may be snapped together with other disk supports 620 in a similar fashion to that shown in FIG. 15. Some examples of possible shapes include rods, tubes, rings, spheres, beads, sheets, etc. If disk support 620 were instead a ring (not shown) with spokes 660 and mesh material inside the ring, then the mesh could be suspended in aperture 610 and operate as the functionalized solid-phase support. FIG. 6 also displays a rounded ridge 630 formed on plate 600 and ridge seat 640 which together provide a plate-to-plate sealing mechanism for preventing cross contamination of wells.

Figure 7:
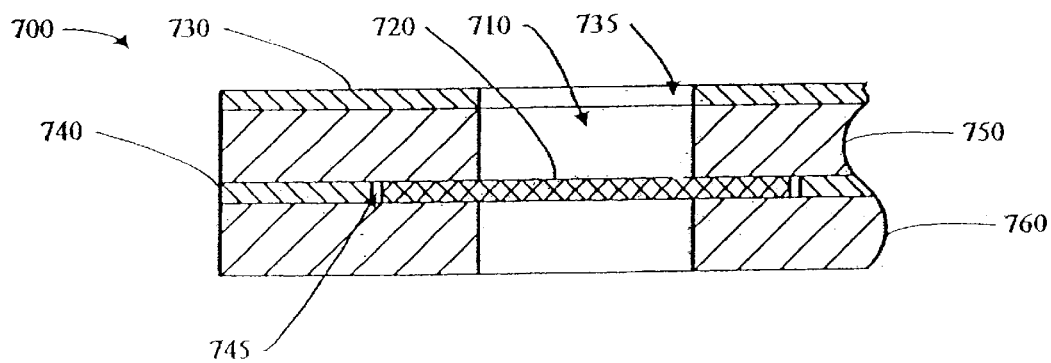
FIG. 7 is a cross-sectional view a mesh support suspended in a plate aperture.

FIG. 7 also displays a cross-section view similar to that shown in FIG. 5 except that stackable plate 700 is shown with solid-phase support 720 temporarily suspended in aperture 710 formed through plate 700. As with plate 300 discussed above, mesh support 710 could be fabricated from a wide variety of materials, including those previously listed. Essentially, support 720 is a piece of mesh sandwiched between upper plate 750 and lower plate 760 that, in combination, form plate 700. Such a mesh support 720 may be placed into position in plate 700 after mesh support 720 is functionalized and may be removed from position for cleavage of a synthesized molecule or storage. Alternatively, mesh support 720 and the walls of aperture 710 may be functionalized together after mesh support 720 is positioned. Gasket material 740 between lower plate 760 and upper plate 750 and gasket material 730 on top of upper plate 750 provide a sealing mechanism for preventing cross contamination.

Figure 8:
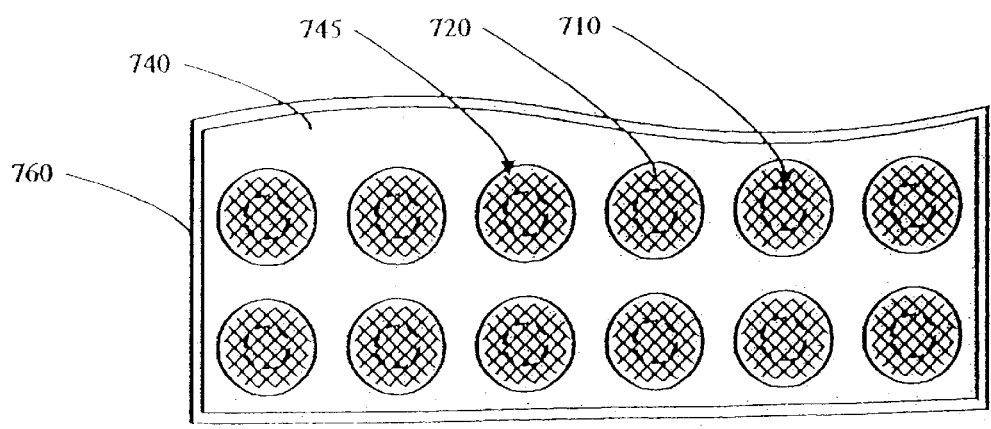
FIG. 8 is a top view of mesh supports and a sealing mechanism on a plate.

FIG. 8 displays a top view of a portion of lower plate 760 with gasket material 740 and mesh support 720 placed thereon. Notably, an aperture 745 larger than aperture 710 is formed through gasket material 740 such that mesh support 720 may be sized larger than aperture 710 and sandwiched between lower plate 760 and upper plate 750 without falling through aperture 710. As shown in FIG. 7, an aperture 735 similar in dimension to aperture 710 is formed through gasket material 730 positioned on top of upper plate 750.

Figure 9:
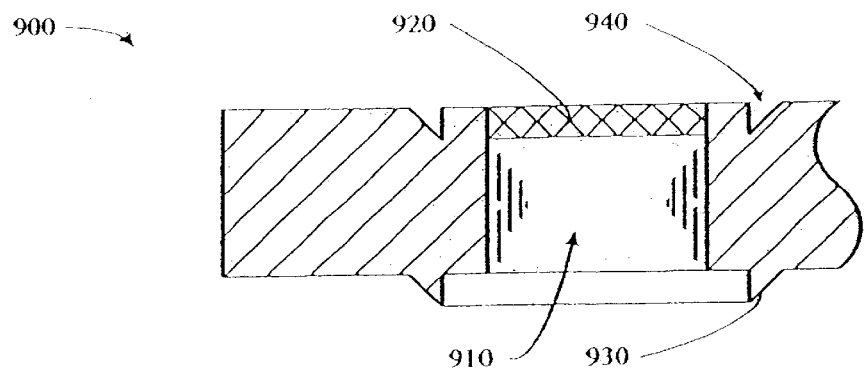
FIG. 9 is a cross-sectional view a mesh support suspended in a plate aperture.
Figure 10:
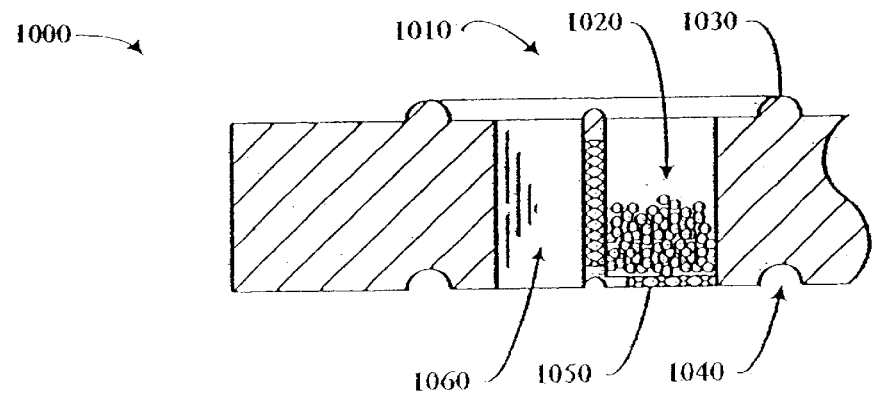
FIG. 10 is a cross-sectional view of bead supports suspended in a plate aperture with a vent.
Figure 11:
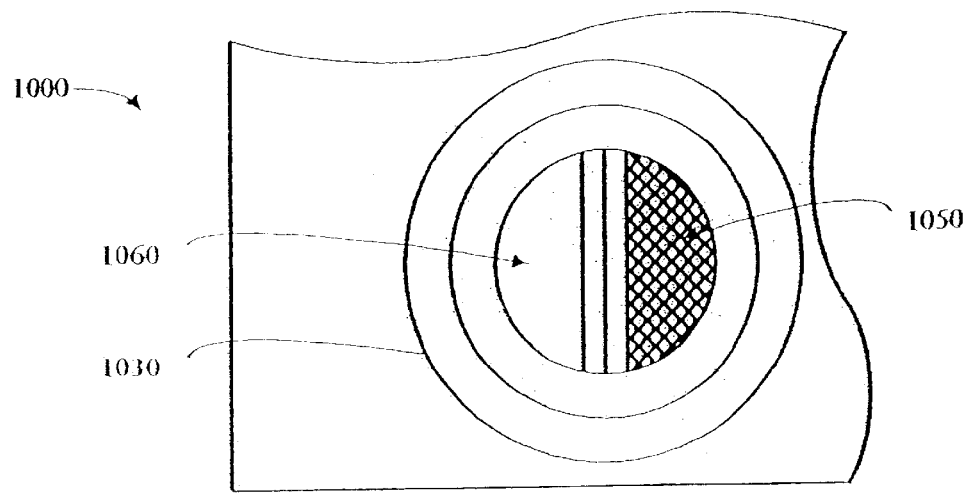
FIG. 11 is a top view of a portion of the plate in FIG. 10.

FIGS. 9–11 display additional embodiments of a stacking plate embodiment. In FIG. 9, plate 900 includes aperture 910, mesh support 920, peaked ridge 930, and ridge seat 940. Mesh support 920 may be formed integrally to plate 900, affixed thereto, rested upon a lip or inset ledge (not shown) formed inside aperture 910, or secured by some other mechanism. Peaked ridge 930 and ridge seat together provide a plate-to-plate sealing mechanism for preventing cross contamination of wells. Alternatively, plate 900 or a similar plate could be inverted such that mesh support 920 is at the bottom of aperture 910 and forms a mesh barrier. Solid-phase bead supports could then be separately placed in aperture 910 to rest on the mesh barrier after the bead supports are functionalized. Such bead supports could be fabricated solely from resin, as is often done in combinatorial chemistry, or from a wide variety of materials, including those previously listed in the discussion regarding plate 300 above. Once the plates are stacked, reagents may be applied to each group of bead supports in the stack since the mesh barrier allows reagents to flow down through stacked apertures 910. Also, it may be possible for any of the plates discussed herein to provide a sealing mechanism by fabricating the plate from a material that forms a seal simply by stacking plates 300 and applying sufficient pressure on the stack.

In FIG. 10 a cross sectional view of another stackable plate is shown and in FIG. 11 a top view of a portion of the plate in FIG. 10 without bead supports is provided. Plate 1000 includes aperture 1010, mesh pocket 1050, and vent 1060, wherein bead supports 1020 are placed in the portion of aperture 1010 sectioned off by mesh pocket 1050. As an example, the vertical portion of mesh pocket 1050 may be a mesh wall dividing a circular aperture 1010 into two semicircles, wherein the horizontal portion of mesh pocket 1050 forms a bottom of one semicircle. The other semicircle is left open to provide vent 1060 such that reagents may pass easily through aperture 1010 in plate 1000. The mesh pocket preferably combines solid portions to provide structural support and mesh panels to provide flow through of reagents. FIG. 10 also shows plate 1000 having a sealing mechanism including rounded ridge 1030 and ridge seat 1040 as described above for FIG. 6. In addition, mesh pocket 1050 includes a similar sealing mechanism since the top of the horizontal portion of mesh pocket 1050 provides a rounded ridge and the bottom of the horizontal portion provides a corresponding ridge seat.

Figure 12:
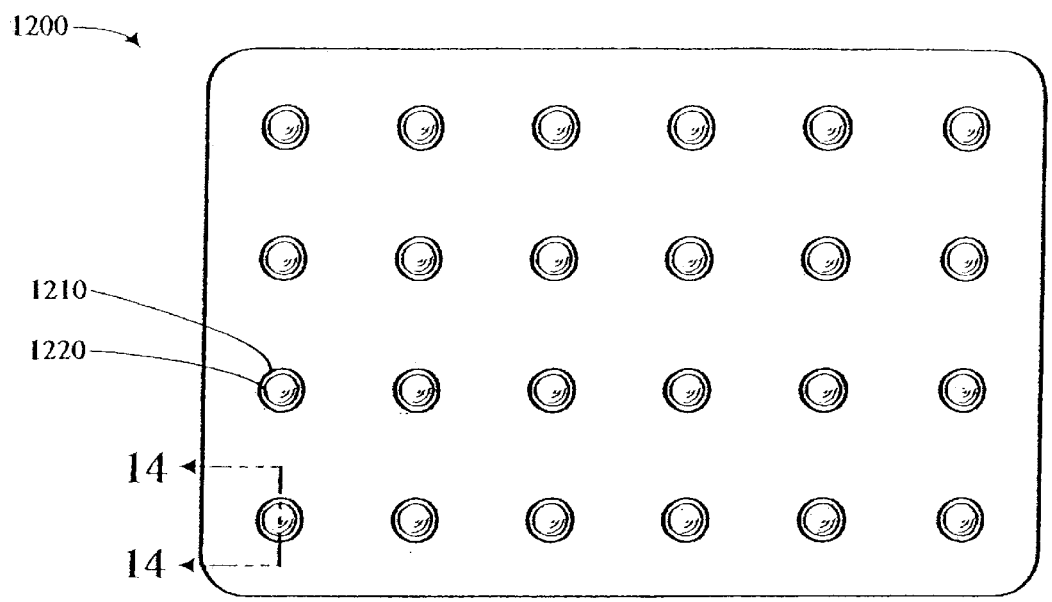
FIG. 12 is a top view of bead supports forming a 3D array in wells.

According to another preferred embodiment of the present invention, parallel synthesis of a library of molecules with 3D diversity may be carried out on a plurality of discrete supports arranged in columns in one or more wells. FIG. 12 shows one example of the preferred embodiment in a top view of a well plate 1200 including wells 1210, wherein wells 1210 contain functionalized solid-phase bead supports 1220 arranged in a 3D array such that parallel synthesis of a library of molecules with 3D diversity is provided. Well plate 1200 includes a four by six 2D array of wells 1210, wherein the number of wells 1210 in well plate 1200 may be modified as needed. For example, well plate 1200 may provide 96 wells 1210 that are spaced to accommodate equipment typically used in combinatorial chemistry, such as equipment adapted for use with standard 96-well plates and other plates with a different number of wells. Also, well plate 1200 may be a standard 96-well plate or other standard well plate provided it is operable according the principles described herein.

In general, bead supports 1220 might be fabricated from any type of glass, plastic, or other material that can be functionalized to provide a solid-phase support and that meets the standards and criteria needed for apparatus used in combinatorial chemistry as determined by those skilled in the art. Exemplary materials include pharmaceutical grade glass, silica gel, alumina gel, cellulose, polyolefins, polypropylene, polyethylene, halogenated polyolefins, TEFLON (polytetrafluoroethylene available from E. I. Du Pont de Nemours and Co. in Wilmington, Del.), resin coated on or adhered to the listed materials and other structurally supportive materials, combinations of the listed materials, etc. In addition, bead support 1220 may be other than a spherical support. For example, it may be that bead support 1220 has perforations formed through it such that greater surface area is provided or is shaped to accommodate easy flow of reagents around or through bead support 1220. Some examples of possible shapes include those shown in FIGS. 14–17 and other rods, tubes, rings, spheres, beads, sheets, etc. The diameter of bead supports 1220 or other shaped supports is preferably about 0.5 millimeter (mm) to 20 mm, but could range from 1 micrometer ($\mu$m) to 5 centimeters (cm). It is also conceivable that supports could be less than 1 $\mu$m in diameter if the technology existed to manipulate supports of such a small size. Even within the preferred range of 0.5 mm to 20 mm supports, stacking and manipulation of supports becomes more difficult as size decreases. The top view of wells 1210 shown in FIG. 3 indicates that the openings into wells 1210 are circular, however, wells 1210 may possess any other shape suitable for accepting supports 1220. For example, the openings of wells 1210 may provide one or more channels (not shown) formed in the sides of wells 1210 to accommodate easy flow of reagents around supports contained in wells 1210.

Figure 13:
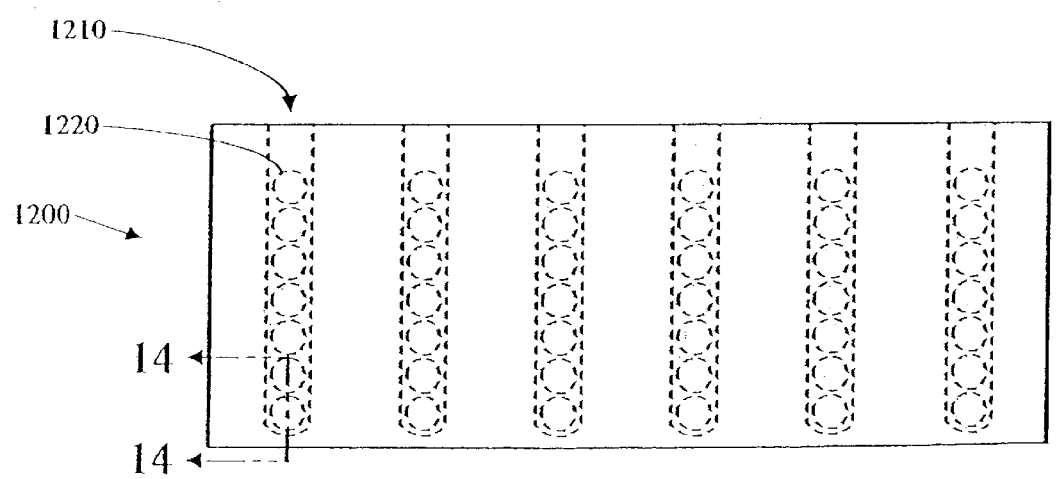
FIG. 13 is a side view of bead supports forming a 3D array in wells.

FIG. 13 shows a side view of well plate 1200. Noticeably, bead supports 1220 are arranged as columns of discrete supports, with one column per well. Alternative arrangements are also conceivable wherein a well is designed to accommodate (not shown) a plurality of columns. One example of such a well plate might include parallel troughs as the wells, wherein a plurality of columns may occupy each well, rather than wells designed to accommodate only one column of supports 1220. Each support 1220 in FIG. 12 is discrete, meaning that each support 1220 is individually separate from all other supports 1220. Such a feature may be helpful, although is not required, in retrieving selected molecules from their respective locations in a 3D array arranged in well plate 1200. Since each support 1220 defines one location in the 3D array, retrieving one support may constitute retrieving a selected molecule from the 3D array.

Well plate 1200 shown in FIGS. 12 and 13 is a generic well plate simply including a 2D array of wells 1210. Other well plates are available in the art that may work equally as well, or better, than generic well plate 1200. For example, a filter plate (not shown) is similar to well plate 1200 except that a filter plate has an orifice formed in the bottom of each well 1210 into which some sort of filter has been inserted. The filter material allows reagents applied at the top of each well to easily drain through the bottom of each well when desired. If only an orifice were placed in the bottom of the well, then supports 1220 could fall through or plug the orifice. Instead, the orifice may be sized such that reagents easily flow around support 1220 at the bottom of well 1210 and through the filter material in the orifice. One type of common filter material is a frit, that is, a porous disk made from glass or other vitreous material and shaped to fit snugly into an orifice formed in the bottom of well 1210 in a filter plate (not shown). Well plate 1200 may also be fitted with various other apparatus that adapt it to use with specific types of devices, including automated devices, for distributing reagents among wells 1210. For example, it is common to cover the openings to wells 1210 with a septum such that contaminants are kept out of wells 1210, yet reagents may be injected from a needle pushed through the septum.

Figure 14:
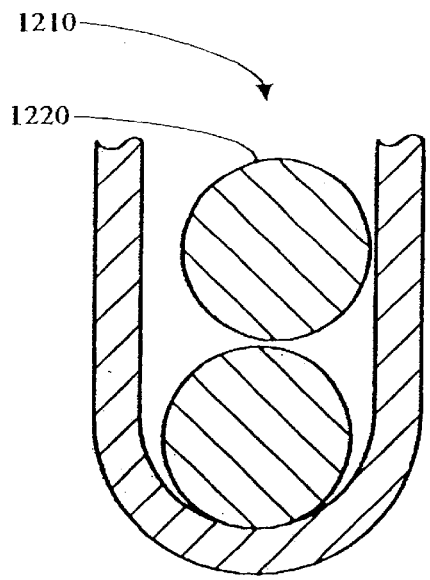
FIG. 14 is a cross-sectional view of two bead supports in a well in FIGS. 12 and 13 taken along lines 14—14.

FIG. 14 is a cross sectional view of two supports 1220 in a portion of well 1210 taken along line 14—14 as indicated in FIGS. 12 and 13. FIG. 14 shows that supports 1220 are sized to allow flow of reagents between the walls of well 1210 and supports 1220. Essentially, reagents need to contact the functionalized surfaces of supports 1220 whereon molecules are to be synthesized. A gap between the walls of well 1210 and supports 1220 may also be helpful, although is not required, in removing supports 1220 from well 1210.

Figure 15:
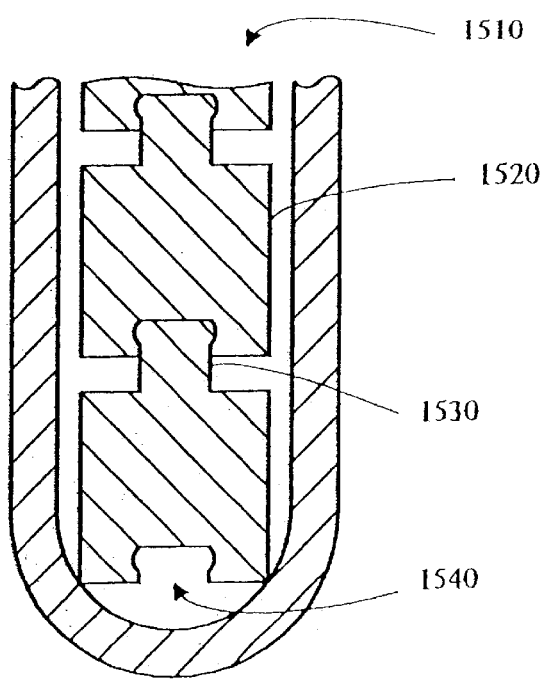
FIG. 15 is a cross-sectional view of two supports coupled together in a well.
Figure 16:
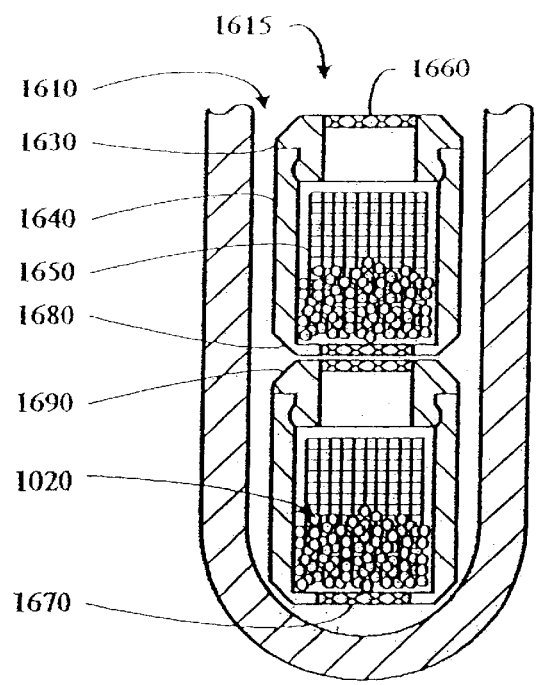
FIG. 16 is a cross-sectional view of beads contained in porous enclosures that are stacked in a column in a well.
Figure 17:
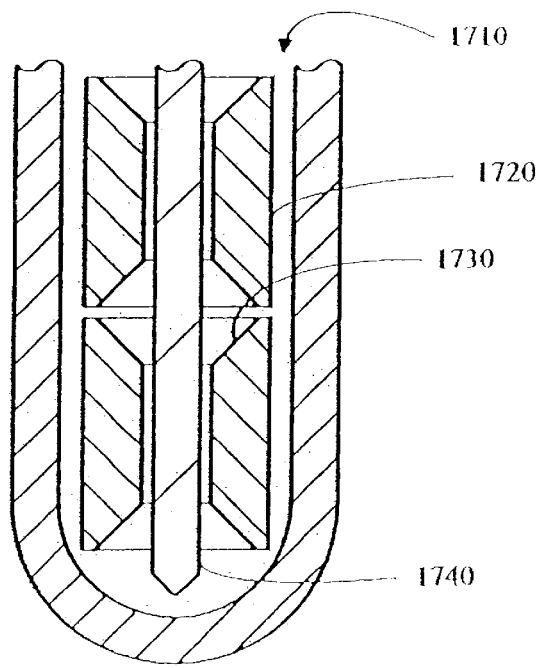
FIG. 17 is a cross-sectional view of two tube supports in a well with a rod inserted through the tubes.

FIGS. 15–17 provide a few examples of several variations that could be made to the basic embodiment of discrete functionalized supports stacked in a column as shown in FIG. 14. FIG. 15 shows a well 1510 in which coupled supports 1520 are stacked in a column. A plug-in-socket type of coupling is displayed for supports 1520 in FIG. 15, however, many other types of couplings may be used. For coupled supports 1520, a plug 1530 of a support 1520 is inserted into a socket 1540 of an abutting support 1520. As with bead supports 1220 discuss above, coupled supports 1520 could be fabricated from a wide variety of materials, including those previously listed. However, if coupled supports 1520 are fabricated from resin, then a coupling mechanism not made from resin will probably be required since resin is typically not a suitable structural material. There may be several advantages to providing coupled supports 1520, for example, one advantage is to allow more orderly stacking of supports 1520 in a column. That is, the column is aligned so that each support 1520 is positioned directly above each support 1520 below it. By contrast, each support 1220 in well 1210 is offset slightly from each support 1220 below it. It may be desirable to align supports 1520 in a column to guarantee even distribution of reagents about supports 1520. Another advantage to providing coupled supports 1520 is to allow all supports in a single column to be lifted from well 1510 together. This feature may be desirable to enable more simple handing of supports 1520 or transfer of a column of supports 1520 to another well. Supports 1520 in FIG. 15 provide both the aligning and the lifting feature with their plug-in-socket type of coupling. Other types of acceptable couplings might provide only an aligning feature or only the lifting feature, depending on preferences for the particular application.

FIG. 16 shows a well 1610 in which one example of porous enclosures 1615 are stacked in a column. Discrete bead supports 1020 are placed inside cylindrical porous enclosures 1615 to provide solid-phase support for parallel synthesis of molecules. Cylindrical porous enclosure 1615 includes a lid 1630 and a cup 1640 which, at least in FIG. 16, have mesh wall 1650, mesh top 1660, and mesh bottom 1670 so that reagents may flow in and out of porous enclosure 1615 to contact bead supports 1020. Various other designs for a porous enclosure 1615 within the scope of the present invention are conceivable and, essentially, should provide a mechanism to contain a group of discrete bead supports 1020 in an enclosure while still allowing contact of reagents with bead supports 1020. For example, a porous enclosure could also be a mesh sheet folded into an envelope shape (not shown) and sealed around its edges with bead supports 1020 inside. Also, the porous enclosures could be substantially as shown except without a lid 1630, wherein such porous enclosures (not shown) are coupled together and the bottom of each enclosure also operates as a lid for the enclosure below it. For porous enclosure 1615 shown in FIG. 16, separate lid 1630 is provided to completely enclose cup 1640 separate from any other porous enclosure 1615. The beveled bottom 1680 and beveled lid 1690 are provided to enable transfer of porous enclosure 1615 using a support transfer device that is discussed below.

FIG. 17 shows yet another type of solid-phase support, a tube support 1720, stacked in a column in well 1710 with a rod 1740 inserted through tube supports 1720. Tube support 1720 optionally has beveled openings 1730 to allow easier insertion of rod 1740 through tube support 1720. Tube support 1720 may be fabricated from various materials as discussed above for other supports and may be functionalized on the outside of the tube, inside of the tube, or both. Rod 1740 may serve several functions, such as, assembling tube supports 1720 into a column before placement in well 1710 and maintaining a column when tube supports are removed from well 1710. Assembling a column and maintaining a column of supports may be helpful, although is not required, in assigning and retrieving selected molecules from individual locations in the 3D array. Rod 1740 may also be used to suspend supports, such as tube support 1720, in well 1710 by providing an end cap (not shown) on the tip of rod 1740 shown extending through the bottom of the column of tube supports 1720. That is, such an end cap retains tube supports 1720 on rod 1740 so that the entire column of tube supports 1720 may be easily placed in and removed from well 1710. Rod 1740 could also be used to suspend porous enclosure 1615 in well 1610 if an apparatus on porous enclosure 1615 is provided to couple it somehow to rod 1740.

Figure 18:
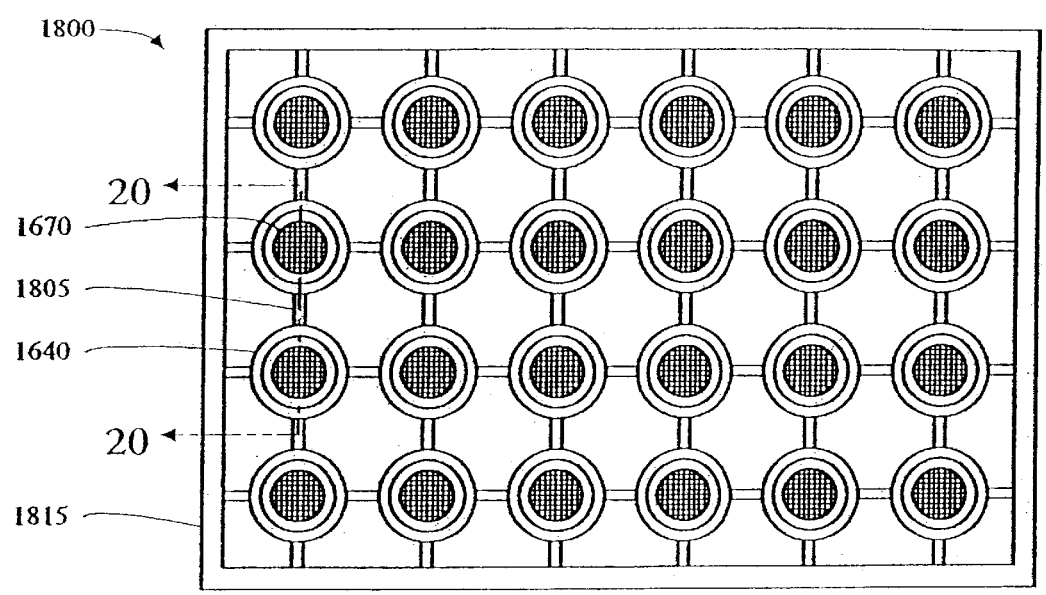
FIG. 18 is a top view of twenty-four baskets for porous enclosures secured in a two-dimensional (2D) framework.

FIG. 18 displays a top view of a 2D framework 1800 of cups 1640, such as those shown in FIG. 16, wherein cups 1640 and outside frame 1815 are interconnected by links 1805. Mesh bottom 1670 of cups 1640 is readily apparent in FIG. 18. Fabricating cups 1640 in 2D framework 1800 should provide easier handling of porous enclosure 1615. For example, cups 1640 may be spaced in framework 1800 to match the spacing of wells 1210 in well plate 1200. Accordingly, the same devices used to deposit bead supports 1020 in a well plate 1200, as is done conventionally, may be used to deposit bead supports 1020 in framework 1800 of cups 1640. Also, if lids 1630 are also fabricated in a framework, then all lids 1630 needed to enclose all cups 1640 in framework 1800 may be positioned together and coupled in place.

Figure 19:
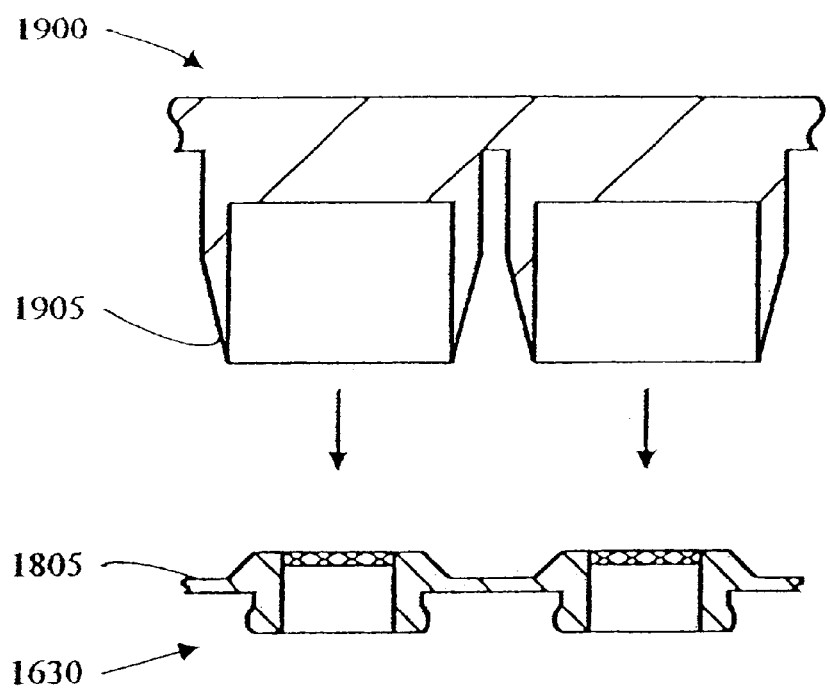
FIG. 19 is a cross-sectional view of two lids for porous enclosures being removed from a 2D framework using a cutting tool.
Figure 20:
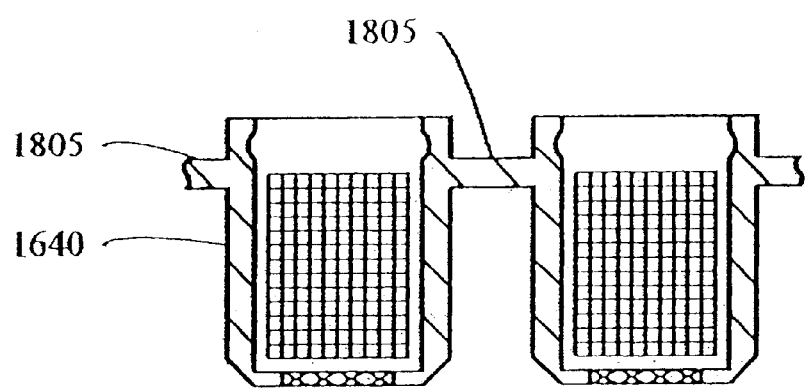
FIG. 20 is a cross-sectional view of two baskets in FIG. 18 taken along line 20—20.

FIG. 20 displays a cross sectional view of two cups 1640 in framework 1800 taken along line 20—20 shown in FIG. 18. Essentially, cups 1640 in FIG. 20 are the same as cups 1640 in FIG. 16 but are shown with links 1805 forming framework 1800 and without lids 1630 and bead supports 1020. Similarly, FIG. 19 displays a comparable cross sectional view of lids 1630 in a 2D framework (not fully shown) similar to framework 1800. FIG. 19 also displays a cutting tool 1900 with edges 1905 sized and positioned to allow simultaneous trimming of links 1805 away from lid 1630. That is, even though lids 1630 are fabricated in a framework, they may be quickly removed using cutting tool 1900. Further, cutting tool 1900 may be used to quickly load porous enclosures 1615 into wells 1610 of a well plate (not shown). First, functionalized bead supports 1020 are placed in all cups 1640 of framework 1800, then lids 1630 in their own framework (not fully shown) are positioned over cups 1640 and coupled thereto, creating porous enclosure 1615. Next, the frameworks are placed such that one porous enclosure is positioned in the opening of each well 1610 in a well plate. Finally, cutting tool 1900, with sufficient edges 1905 to trim each porous enclosure 1615 from framework 1800 and the lid framework, is positioned over such frameworks. As cutting tool 1900 is depressed, it first trims lids 1630 and then trims cups 1640, allowing porous enclosures 1615 to drop into well 1610. The process may be repeated to stack porous enclosures 1615 into columns in wells 1610, thus creating a 3D array of solid-phase supports adapted to provide parallel synthesis of a library of molecules with 3D diversity.

Figure 21:
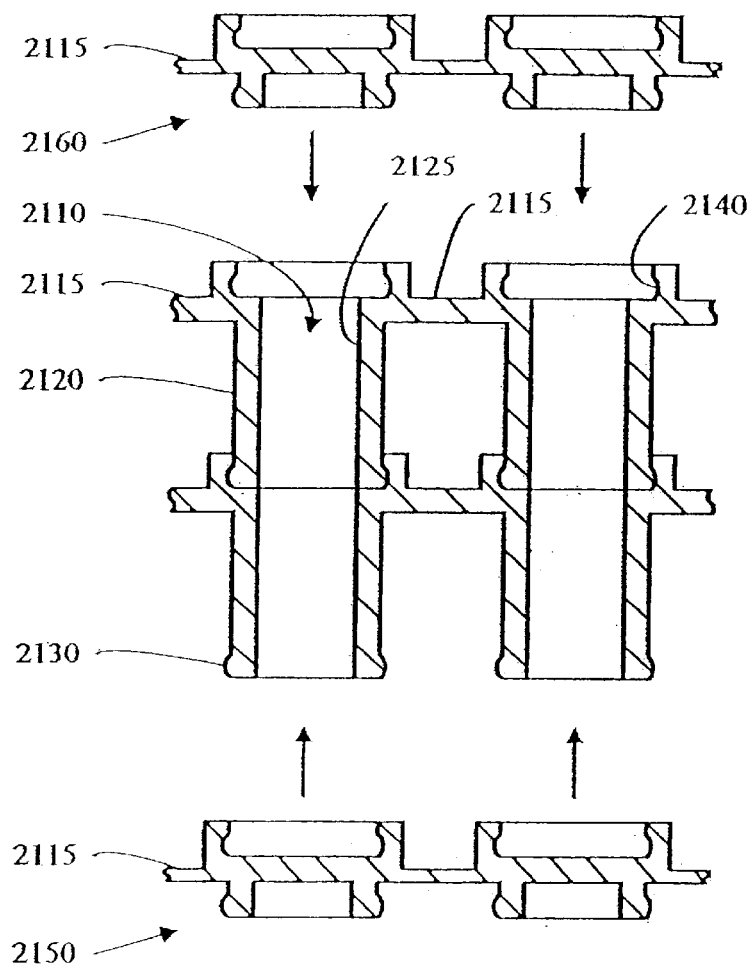
FIG. 21 is a cross-sectional view of stacked tube supports secured in 2D frameworks being joined with two end caps and two lids also in 2D frameworks.

The embodiment of a framework, as shown in FIG. 18, may also be adapted to provide other 3D arrays within the scope of the present invention. Accordingly, in another preferred embodiment of the present invention, parallel synthesis of a library of molecules with 3D diversity may be carried out in stacked 2D frameworks of tubes, wherein the supports include either the walls of tubes, supports suspended within the tubes, or both. FIG. 21 shows one example of the preferred embodiment in a cross sectional view of two tiers of two tube supports 2120 wherein each tier is fabricated in a 2D framework (not fully shown) by providing links 2115 between tube supports in the same fashion with which cups 1640 were fabricated in framework 1800 shown in FIG. 18. Inner walls 2125 of tube supports 2120 may be functionalized to provide a solid support for synthesis of molecules. Also, with inner walls of tube supports 2120 substantially aligned, a well 2110 for delivering reagents and synthesizing such molecules is provided. Tube supports 2120 are fabricated from the same materials suitable for other supports described herein, although resin alone probably does not provide sufficient structural support unless combined with a structural material. Even though tube supports 2120 use the embodiment of a framework, they are analogous to stackable plate 300 and the stacking plate embodiment shown in FIGS. 3–11. Accordingly, each variation of the stacking plate embodiment discussed herein is also applicable to tube supports 2120 in a 2D framework. That is, each of the sealing mechanisms and various solid supports used in the stacking plate embodiment of FIGS. 3–11 may be incorporated into the stacking tube framework embodiment.

In FIG. 21, one tier of tube supports 2120 in a framework is stacked on top of another tier of tube supports 2120 also in a framework. A sealing mechanism is provided to temporarily join the abutting top and bottom tube supports 2120. For the example shown, the sealing mechanism includes the bottom of tube support 2120, acting as a plug 2130, that is inserted into the top of a tube support 2120, acting as a socket 2140. Multiple other sealing mechanisms in keeping with the present invention are also conceivable. Also, several differently shaped tube supports 2120 are in keeping with the present invention. Tube supports 2120 with a circular openings are probably preferred since much of the equipment used in combinatorial chemistry is designed with well plates having circular openings in mind. Nevertheless, openings with another shape may be acceptable, such as a square or those shapes designed to provide inner walls 2125 with a greater surface area than possible with a circular opening of comparable size. For example, a star-shaped tube support 2120 opening is one possibility.

FIG. 21 also shows end cap 2150 being coupled to the bottom tier of tube supports 2120 using a plug-in-socket type of sealing mechanism to an end wall of each well 2110. End caps 2150 are similarly joined in a 2D framework (not fully shown) by links 2115 between individual end caps 2150. At least for the devices shown in FIG. 21, the same structure used for end caps 2150 is adapted to also operate as optional lids 2160, however, this feature is not required. Cross contamination is not as significant of a concern in the stacking tube embodiment of FIG. 21 as it is in the stacking plate embodiment discussed above. Accordingly, a sealing mechanism in stacked tube supports 2120 primarily prevents leaking of reagents outside wells 2110. Also, optional lids 2160 act as a sort of splash guard to prevent splashing or spilling of reagents from one well 2110 to another. Although not shown, draining orifices may also be formed through end caps 2150 such that application of a vacuum to the orifices quickly drains reagents from each well 2110. Further, a septum may be formed in each lid 2160 to prevent spilling yet allow injection of reagents through such a septum.

Figure 22:
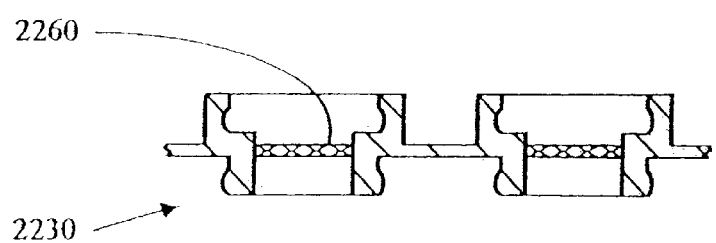
FIG. 22 is a cross-sectional view of linking mesh caps in a 2D framework.

FIG. 22 shows a mesh coupler 2230 that may be used with an alternative embodiment of FIG. 21 (alternative not shown). Essentially, instead of tube support 2120 being completely open at both ends, a mesh barrier (not shown) that is permeable to reagents may be provided in each tube support 2120. Such an apparatus is similar in concept to the apparatus shown in FIG. 10. Accordingly, bead supports 1020 may rest on a mesh barrier (not shown) in a tube joined in a framework, wherein molecules are synthesized at least on bead supports 1020 and potentially on inner walls of the tube as well. Once bead supports 1020 are placed in such a tube, other tube frameworks may be stacked on top to assemble a 3D array of solid supports. During the process of stacking or unstacking the tube frameworks, it is possible to spill the small beads, thus, mesh coupler 2230 or a similar device may be used to cap each tier of tube frameworks and to prevent spilling. Barrier 2260 in mesh coupler 2230 allows reagents to flow through the well (not shown) formed by the stacked tubes and synthesize molecules on supports 1020 with 3D diversity. In keeping with the terminology used above, a tube with a mesh barrier constitutes one example of a porous enclosure. Such a porous enclosure, however, has non-porous side walls (walls of the tube) that, when stacked in alignment with other such porous enclosures, form side walls for a well. It is conceivable that various other porous enclosures in a framework that are capable of containing bead supports in a 3D array and being stacked to form a well may be designed in keeping with the present invention.

Figure 23:
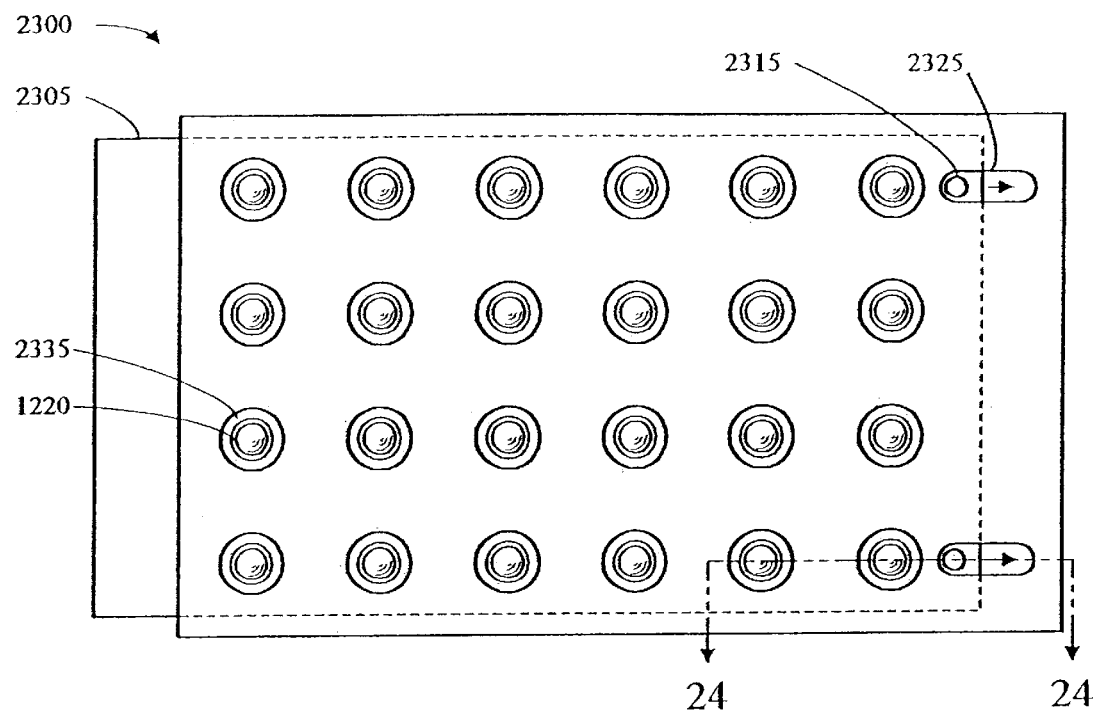
FIG. 23 is a top view of a transfer block having one gate with the gate in an open position.

In another preferred embodiment of the present invention, parallel synthesis of a library of molecules with 3D diversity may be assisted by using a support transfer device adapted to enable transfer of supports used in a 3D array and to maintain the ability to retrieve selected molecules their respective locations. FIGS. 23–29 show a few examples of the preferred support transfer device that are particularly useful with the 3D arrays disclosed by FIGS. 12–17 and alternative embodiments thereof. FIG. 23 shows a top view of a transfer block 2300 which includes sliding gate 2305, two guide pins 2315, two guide slots 2325, and a four by six 2D array of recesses 2335. Gate 2305 is in an open position in FIG. 23. Guide pins 2315 are attached to gate 2305 and positioned in guide slots 2325 such that movement of guide pins 2315 in the direction indicated moves gate 2305 into a closed position (not shown). FIG. 23 also shows bead supports 1220 placed in recesses 2335 in anticipation of transferring bead supports 1220 to a 3D array or after transfer from a 3D array. Notably, gate 2305 of transfer block 2300 may be moved from an open to closed position or vice versa by either grasping gate 2305 itself or by grasping guide pins 2315 attached to gate 2305.

Figure 24:
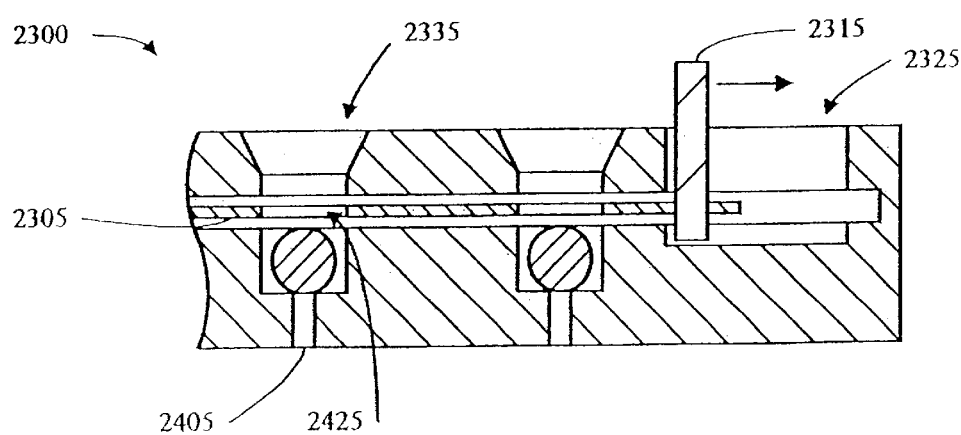
FIG. 24 is a cross-sectional view of the transfer block in FIG. 23 taken along line 24—24 with the gate in a open position.

FIG. 24 shows a cross sectional view of transfer block 2300 taken along line 24—24 as shown in FIG. 23. With gate 2305 in an open position it can be seen that supports 1220 may pass through gate 2305 through apertures 2425 formed therein. Also, recesses 2335 optionally provide a beveled opening to assist supports 1220 in entering recess 2335. Transfer block also optionally includes vacuum orifices 2405 to further assist supports in entering recess 2335 by allowing the withdrawal of air from recesses 2335, thereby suctioning supports 1220 into recesses 2335. Although supports 1220 are shown as spherical in FIGS. 23–27, the supports actually used may possess any number of shapes, such as those discussed herein. In trying to load transfer block 2300, gate 2305 is placed in an open position and supports are placed on the top of transfer block 2300. Supports 1220 shown in FIGS. 23 and 24 will probably fall into recesses 2335 rather easily since they are spherical. However, other supports, such as coupled supports 1520 or tube supports 1720, may need additional assistance, thus, beveled openings and vacuum orifices 2405 may be helpful, but are not required. Also, supports may be designed with features (not shown) such as a size and shape that encourage entering recesses 2335 in a specified orientation.

In keeping with the terminology of FIGS. 1 and 2, and entire Z plane of supports 1220 can be quickly and easily loaded into transfer block 2300. Once supports 1220 are loaded, gate 2305 may be closed by sliding it in the direction indicated. As can be seen from FIGS. 23 and 24, moving gate 2305 into a closed position will relocate apertures 2425 such that any excess supports 1220 in recess 2335 will be separated from the one support 1220 at the bottom of each recess 2335. Once gate 2305 is in the closed position, excess supports 1220 may be removed while supports 1220 inside recess 2335 are withheld from passing through gate 2305. Since supports may be selected from several different shapes and sizes, if given supports are to be used in transfer block 2300 or a related device, then allowance should be made to provide separation of supports with by a gate. For this reason, porous enclosures 1615 in FIG. 16 are provided with beveled bottom 1680 and beveled lid 1690. Otherwise, it would be difficult to separate porous enclosures 1615 with a gate.

Transfer of supports 1220 to a 3D array occurs by inverting transfer block 2300, aligning recesses 2335 with locations in a 3D array, such as wells 1210 in well plate 1200, and moving gate 2305 to an open position. Supports 1220 will then fall into the 3D array locations and establish a Z plane of supports therein. Such a transfer block is extremely useful in arranging a 3D array particularly when each support 1220 in the Z plane possess the same $R_1$ building block.

The process of unloading supports 1220 from a 3D array using transfer block 2300 is conducted by inverting transfer block 2300, placing it on a 3D array of discrete supports 1220, and turning over both the 3D array and transfer block such that the 3D array is inverted and transfer block 2300 is upright. Supports 1220 will fall into open recesses 2335 and the gate 2305 may be closed, withholding one Z plane of supports. Both the 3D array and transfer block 2300 are turned over again so that the 3D array is then upright and supports 1220, less the top Z plane of supports 1220, may fall back into position.

Figure 25:
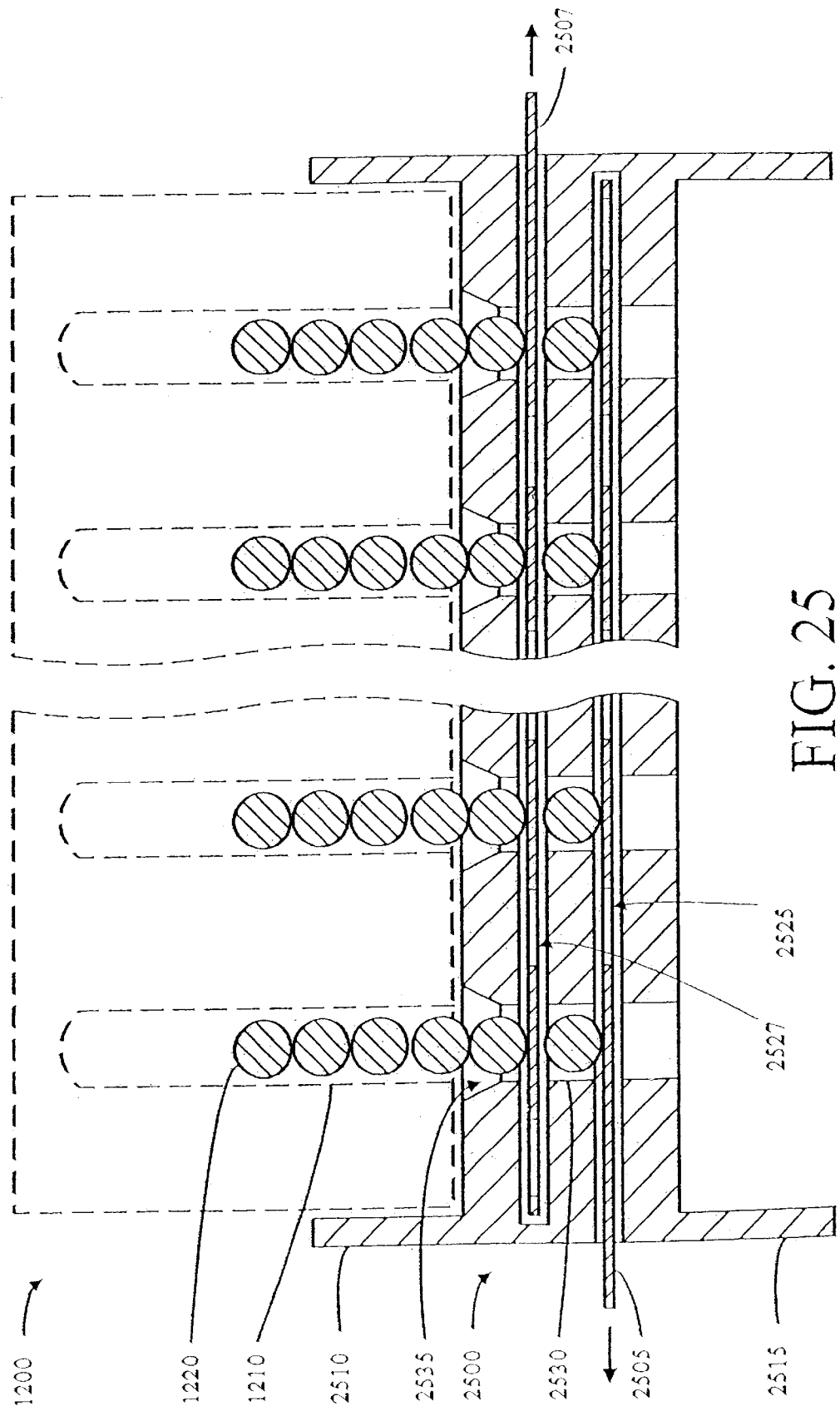
FIG. 25 is a cross-sectional view of a transfer block with a top gate and a bottom gate.

Alternative embodiments of a support transfer device in keeping with the present invention are conceivable, such as a transfer block 2500 shown by cross sectional view in FIG. 25 having a bottom gate 2505 instead of vacuum orifices 2405 shown in FIG. 24. Such a bottom gate 2505 selectively closes off a bottom exit from recesses 2535 that pass completely through the transfer block. That is, a bottom gate 2505 is in a closed position when loading supports 1220 into transfer block 2500, but is moved to an open position to allow supports 1220 to fall out the bottom of transfer block 2500 and into a 3D array.

In FIG. 25, transfer block 2500 is shown in association with well plate 1200, wherein well plate 1200 is inverted and rests on top of transfer block 2500. A top retaining wall 2510 formed around the edge of transfer block 2500 is sized to register well plate 1200 against transfer block 2500 such that wells 1210 align with recesses 2535. With wells 1210 and recesses 2535 aligned, supports 1220 may be loaded into recess 2535 by dropping through apertures 2527 in top gate 2507, when in an open position, and resting on bottom gate 2505 in its closed position. Top gate 2507 may then be closed to segregate the columns of supports 1220 from the bottom Z plane of supports 1220. Accordingly, one segregated support 1220 will then be present in the unloading portion 2530 of each recess 2535. The Z plane of supports 1220 may then be unloaded into another apparatus for cleavage, storage, etc. by moving bottom gate 2505 to an open position and allowing supports 1220 to drop through apertures 2525. Transfer block 2500 also includes a bottom retaining wall 2515 to assist in registering transfer block 2500 with other apparatus, such as another well plate (not shown) positioned below transfer block 2500. An aperture (not shown) may optionally be formed through each of retaining walls 2510 and 2515, allowing supports 1220 to be drained off transfer plate 2500 through the aperture into another container. Also, although transfer block 2500 is not shown with guide pins and guide slots as transfer block 2300 in FIGS. 23 and 24, such features and other features may be incorporated into transfer block 2500 if desired.

In addition to the use described above, transfer block 2500 is also useful in loading functionalized supports 1220 into well plate 1200 for synthesis of molecules. Preferably, an excess of supports 1220 needed to create one Z plane of supports is placed on top of transfer plate 2500. Top retaining wall 2510 prevents spilling of supports 1220 while transfer block 2500 is jostled such that at least one support 1220 is in each recess 2535. If needed, then top gate 2507 may be used to segregate one Z plane of supports 1220, after which bottom gate 2505 is opened to load supports 1220 into a well plate 1200 (not shown in FIG. 25) preparatory to synthesis.

In addition, yet another alternative embodiment of a support transfer device is a transfer block (not shown) with recesses similar to transfer blocks 2300 and 2500, but with an upper gate, a first lower gate, a second lower gate, and recesses having a unloading portion and a reservoir portion. The unloading portion is sized to receive only one support and resides between the first and second lower gate. The reservoir portion is sized to receive one or more supports and resides between the upper gate and first lower gate. The basic operation of such a transfer block includes opening the upper gate and first lower gate, with the second lower gate closed, and filling the unloading portion and the reservoir portion of the recesses. The upper gate may then be closed and excess supports removed from the top of the transfer block. Also, the first lower gate may then be closed to segregate the multiple supports in the reservoir portion from the one support in the unloading portion. Once the transfer block is positioned over a 3D array, then the second lower gate may be opened to release the one support in the unloading portion. The second lower gate is then closed, the first lower gate is opened to drop another support into the unloading portion, and the first lower gate is reclosed to resegregate the remaining supports in reservoir portion.

The above description of the basic operation of an alternative transfer block is only exemplary since the device may be used in several different aspects of synthesizing a 3D library of molecules by altering and/or reordering the above steps. For example, the transfer block may be loaded only with supports having the same $R_1$ building blocks and then used to load multiple arrays each with one Z plane of such supports. Also, the transfer block could receive an entire 3D array of supports and then be used to load one Z plane at a time into separate well plates for cleavage of synthesized molecules. Further, instead of including a 2D array of recesses, a transfer block could include only a one dimensional array of recesses, in other words, only one row of recesses. Thus, such a transfer block would be capable of loading only one row of a Z plane at time, however, it may be useful when certain rows of a given Z plane are to contain supports with different $R_1$ building blocks. Still other variations are conceivable in keeping with the present invention.

Figure 26:
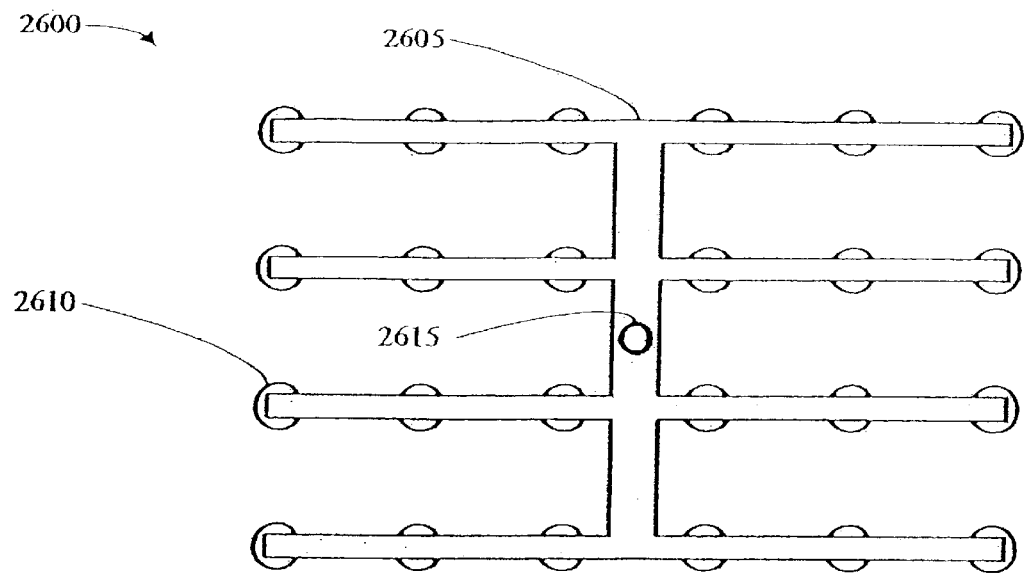
FIG. 26 is a top view of a support transfer device with a twenty-four tubes connected to a vacuum manifold.
Figure 27:
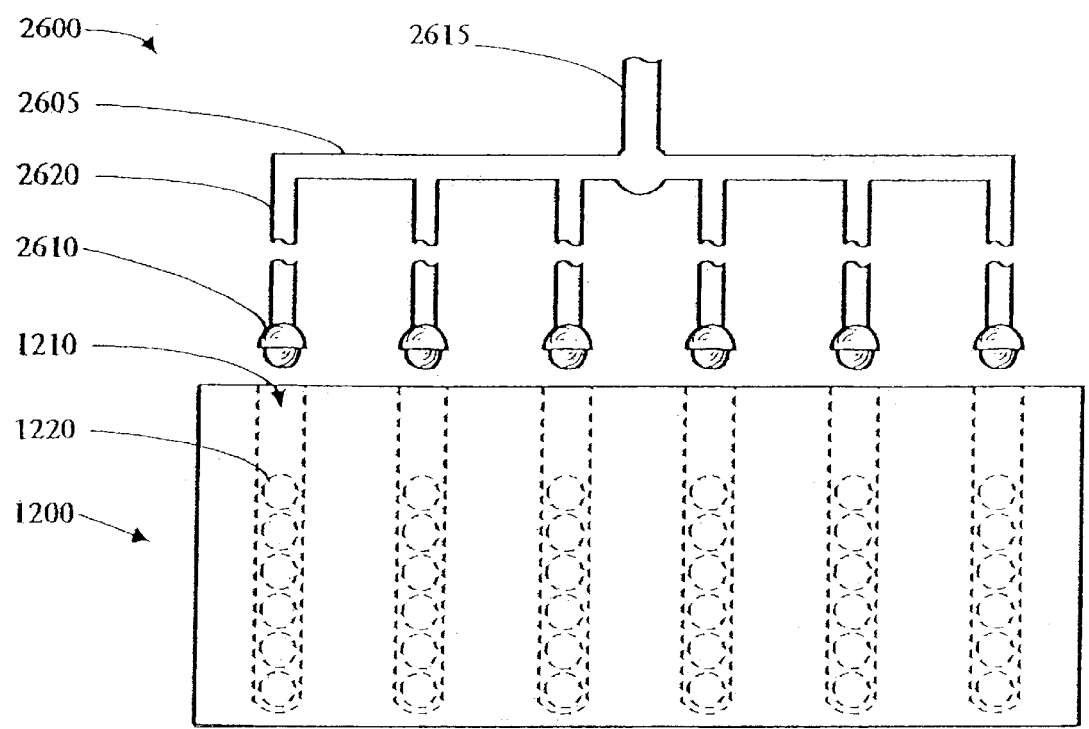
FIG. 27 is a side view of the device in FIG. 26 with supports suctioned from a 3D array of supports.

Turning now to FIG. 26, another example of a preferred embodiment of a support transfer device is shown in a top view of a transfer manifold 2600. Transfer manifold 2600 includes a vacuum manifold 2605, a four by six 2D array of suction cavities 2610, and vacuum supply 2615. FIG. 27 shows a side view of transfer manifold 2600 positioned over well plate 1200 after having removed the top Z plane of supports 1220 from wells 1210. Tubes 2620 are connected at one end to vacuum manifold 2605 and at the other end to suction cavities 2610 such that, when vacuum supply 2615 is applied to vacuum manifold 2605, air withdrawn from suction cavities 2610 withdraws one support 1220 into each suction cavity 2610. Suction cavities 2610 are preferably shaped to correspond to the shape of supports 1220. For example, if porous enclosures 1615 were instead positioned in wells 1210 then suction cavities 2610 would preferably be more cylindrical shaped rather than hemispherical. Transfer manifold provides a simple mechanism for transferring one Z plane of supports at time to or from a 3D array. Multiple alternate embodiments are also conceivable, such as a one dimensional vacuum manifold for transferring one row of supports 1220 at a time. As indicated above, such a device may be useful when certain rows of a given Z plane are to contain supports with different $R_1$ building blocks In FIG. 28, another example of a preferred embodiment of a support transfer device is shown in a top of view of a transfer rack 2800 and FIG. 29 shows a cross sectional view of transfer rack 2800 taken along line 29—29 indicated in FIG. 28. Transfer rack 2800 includes a four by six 2D array of rods 2810 extending up from a platform 2830. Tube supports 2820 similar to tube supports 1720 in FIG. 17 are loaded on rods 2810 of transfer rack 2800, although tube supports 1720 may also be used. Rods 2810 of various sizes and shapes may be alternatively provided in a transfer rack such that supports having various other sizes and shapes may also be loaded onto a transfer rack in a manner similar to that depicted in FIGS. 28 and 29. Even porous enclosures 1615 shown in FIG. 16 could be adapted for use with transfer rack 2800.

Figure 28:
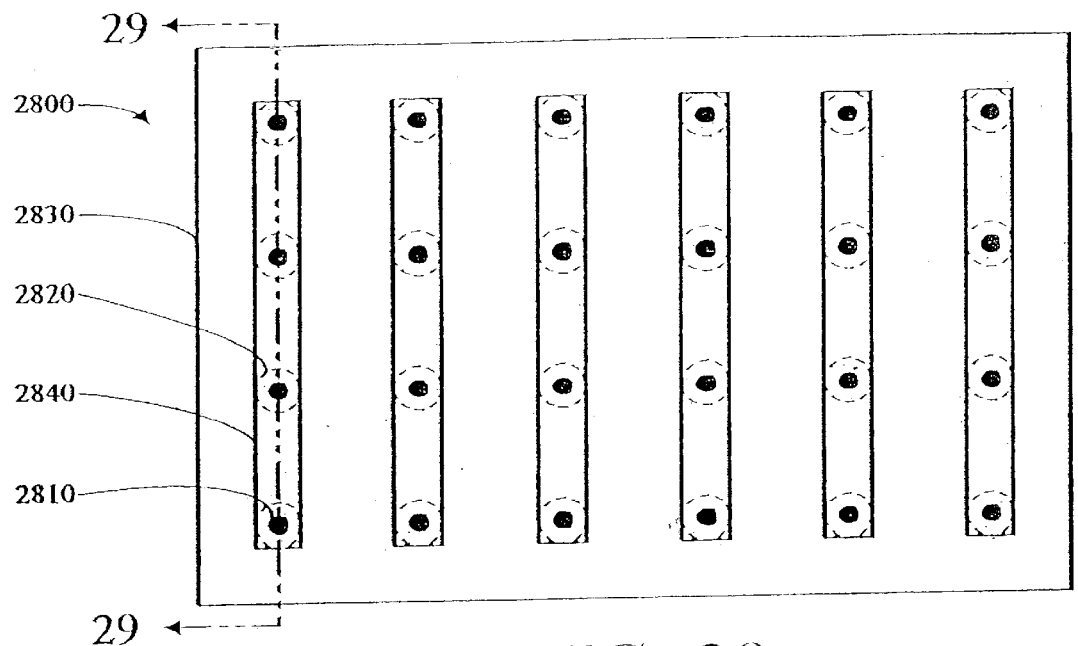
FIG. 28 is a top view of tube supports loaded on a rack having end caps.
Figure 29:
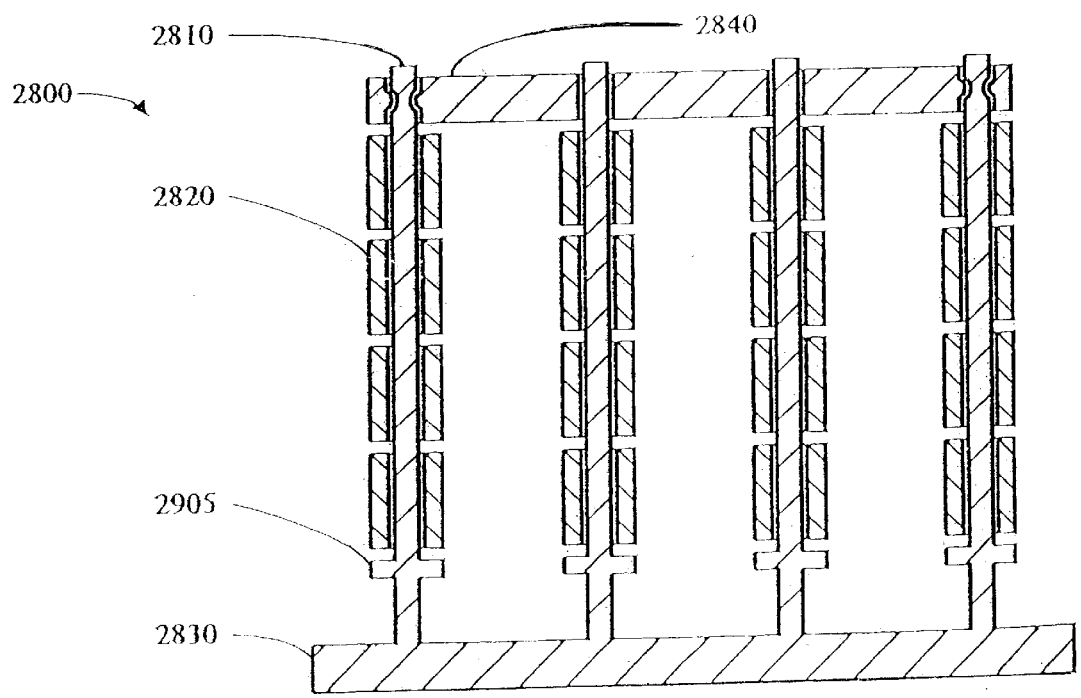
FIG. 29 is a cross-sectional view of the rack in FIG. 28 taken along line 29—29.

FIGS. 28 and 29 also show an end cap 2840 positioned on each row of four rods 2810 to prevent tube supports 2820 from coming off rods 2810. Apertures formed through end cap 2840 receive the tips of rods 2810. Notably, two of the apertures shown in FIG. 29 include a mechanism to retain end cap 2840 on rods 2810 and the other two apertures do not. End cap 2840 may also possess various other shapes and/or sizes, however, consideration should be given to how transfer rack 2800 will be used. Preferably, transfer rack 2800 is used both to transfer tube supports 2820 and to retain tube supports 2820 in a 3D array. That is, tube supports 2820 preferably remain on transfer rack 2800 throughout the synthesis process. For example, one method for accomplishing parallel synthesis using transfer rack 2800 requires using well plates (not shown) having parallel troughs as the wells, wherein a plurality of columns of tube supports may occupy each trough, rather than wells designed to accommodate only one column of tube supports. In keeping with the terminology in the above discussion regarding FIGS. 1 and 2, each parallel trough of such well plates is used to apply selected reagents to each X and Y plane of tube supports in a 3D array on transfer rack 2800. That is, end cap 2840 is positioned on each of the six rows of four rods 2810 as shown in FIG. 28, then transfer rack 2800 is inverted and placed in a six trough well plate, with one row of rods in each trough. Each of the six troughs is filled with one reagent either before or after positioning transfer rack 2880 therein. Thus one reagent is applied to the each X plane of tube supports 2820, meaning each group of tube supports 2820 stacked in columns in a given row of rods 2810.

To apply reagents to each Y plane of tube supports on transfer rack 2800, end caps 2840 are removed and replaced with end caps (not shown) positioned over each of the four rows of six rods in transfer rack 2800. Transfer rack 2800 is then inverted and placed in a four trough well plate filled with reagents, thus applying each reagent to each Y plane of tube supports. Since some support material may be less dense than some liquid reagents used, an obstruction device 2905 that limits movement of the supports may also be needed to keep tube supports 2820 immersed in any liquid reagents in well plate troughs. Obstruction device 2905 may assume various sizes and shapes, FIG. 29 provides just one example. Also, different arrangements of end caps and troughs and different numbers of rods may be provided while staying within the scope of the present invention. For example, it is possible to provide an end cap (not shown) that covers only one rod 2810 such that transfer plate 2800 may be used with well plate 1200 shown in FIG. 12 and only one column of tube supports 2820 is positioned in each well 1210.

Regardless of the end cap structure, transfer block 2500 may be useful in unloading tube supports 2820 from transfer rack 2800. The entire 3D array may be unloaded into transfer block 2500 and then dropped one Z plane at a time into well plates or other apparatus where cleavage or storage of synthesized molecules on tube supports 2820 will occur. Also, other transfer blocks referenced herein according to the present invention may be used to unload one or more Z planes of tube supports 2820 at a time from transfer rack 2800 and place tube supports 2820 in well plates or other apparatus. The various transfer blocks, transfer manifolds, etc. may also be used to load various types of supports onto transfer rack 2800, however, it is preferable to use supports and support transfer devices that allow rods 2810 to be easily aligned with and inserted through such supports. For example, tube support 1720 is adapted to provide easy insertion of rods 2810 therethrough.

Accordingly, the present invention provides various mechanism and systems of combined mechanisms that may be used to implement the invention of a 3D array of solid-phase supports adapted to provide parallel synthesis of a library of molecules with 3D diversity. Now that the basic concept of conducting 3D parallel synthesis and the apparatus for conducting such synthesis have been described, more specific methods for functionalizing supports and conducting such synthesis may be described. In light of the disclosure herein, it will be apparent to those skilled in the art that many of the methods for functionalizing supports and synthesis of molecules in two dimensions, as known in the art, may be modified for use with the present invention. Some of such methods are described in the above patent references that were herein incorporated by reference. In addition, the following examples are provided:

List of Abbreviations

DCM: dichloromethane
DIAD: diisopropylazodicarboxylate
DIC: N,N'-diisopropylcarbodiimide
DMF: N,N-dimethylformamide
Fmoc: 9-flourenylmethyloxycarbonyl
HOBt: 1-hydroxybenzotriazole
HPLC: high performance liquid chromatography
NMR: Nuclear Magnetic Resonance
PP: polypropylene
PS: polystyrene
SPPS: solid phase peptide synthesis
TFA: trifluoroacetic acid
TFMSA: trifluoromethanesulfonic acid
THF: tetrahydrofurane
The abbreviations used for the various amino acids are in accordance with the recommendations of the IUPAC-IUB Comission of Biochemical Nomenclature [J. Biol. Chem., 247, 977–983 (1972)], and refer in all case to L-configuration amino acids.

EXAMPLE 1

General Procedure for Preparation of Polystyrene-Grafted Polypropylene (PP) Ball Styrene (99% purity available from Aldrich Chemical in Milwaukee, Wis.) was passed through basic alumina to remove impurities. If desired, it may additionally be distilled from sodium or from calcium hydride. The purified styrene was combined with methanol to produce a 25% (v/v) styrene solution, then 25 ml of the solution was placed in an ampule together with 0.2 molar (M) sulfuric acid and a polypropylene ball having a 4.7 millimeter (mm) (³⁄₁₆ inch (in)) diameter that had been washed in n-hexane. To thoroughly degas the solution, freeze-thaw cycles on a high vacuum line were repeated and the ampule was then sealed under vacuum. The ampule and its contents were irradiated in a cobalt gamma irradiation facility. The dose rate was approximately 500 Gray/hour (Gy/hr) with a total dose of 5.0 kGy (kiloGray). After irradiation, the ampule was placed on a reciprocating shaker for 24 hours. After the 24 hour time period the ball was extracted in a Soxhelt apparatus with dichloromethane (DCM) and dried.

EXAMPLE 2

Aminomethylation (Functionalization) of Polystyrene-Grafted PP Balls

One hundred 4.7 mm diameter polystyrene-grafted PP balls were placed in a 50 ml solid phase peptide synthesis (SPPS) vessel on a reciprocation shaker and washed with 30 ml of TFA/DCM (1:1 v/v) for 4×5 min (4 times for 5 minutes each). A solution of (2.1 millimoles (mmol)) N-(hydroxymethyl)phthalimide (97% purity available from Acros Organics USA in Pittsburgh, Pa.) in 50 ml of TFA/DCM (1:1 v/v) was added to the pre-washed balls and the mixture was shaken for 20 min. Next, 10 ml of TFMSA/TFA/DCM (10:45:45 v/v/v) was added drop wise over a period of 4–5 hours and shaking was continued for another 4 hours after the addition. The balls were separated from the mixture by filtration and washed sequentially with the following: TFA/DCM (1:1 v/v) (100 ml), DCM (250 ml), methanol (150 ml), and ethanol (150 ml). The balls were then shaken in 50 ml ethanol containing 10% hydrazine (Aldrich) for 12 hours at 70° C. The balls were isolated from the hot mixture and washed sequentially with the following: hot ethanol (50 ml), hot DMF (50 ml), hot ethanol (50 ml), hot methanol (50 ml), and DCM (50 ml). The result was an aminomethyl moiety attached to various aromatic sub-units of the polystyrene-grafted portion of the ball supports. Ultimately, the balls were treated with 50 ml of DIEA/DCM (1:9 v/v) for 2×5 min, washed with 200 ml of DCM and dried at room temperature. Spectrophotometric ninhydrin color tests indicated 2.0 micromole ($\mu$mol) $NH_2$/ ball.

EXAMPLE 3

Attachment of Fmoc-Rink Linker to Aminomethyl Polystyrene-Grafted Polypropylene Ball Support One hundred polystyrene-grafted PP balls functionalized to the aminomethyl functionality (substitution—2.0 $\mu$mol/ball) as described in Example 2, were pre-washed with 150 ml DMF. The balls were placed into a SPPS reaction vessel containing DMF. Fmoc-Rink linker (p-[(R,S)-$\alpha$-[1-(9H-Fluoren-9yl)-methoxyformamido]-2,4-dimethoxybenzyl]-phenoxyacetic acid) (0.6 mmol or 3 equivalents (equiv.)) and HOBt (0.6 mmol or 3 equiv.) were dissolved in DMF and charged into the SPPS reaction vessel. DIC (0.6 mmol or 3 equiv.) was dissolved in 1 ml of DMF and added. The mixture was shaken on a reciprocating shaker at 25° C. for 15 hours. The mixture was filtered and washed with DMF 5×100 ml (5 times with 100 ml each time). The result was that the Fmoc-Rink linker carboxylic acid functionality formed an amide type covalent bond to the amine functionality of the functionalized polystyrene-grafted ball support.

EXAMPLE 4

Attachment of the First Diversity $R_1$ Group Building Block to the Rink Linker Substituted Ball Support Using eight Fmoc-Rink linker substituted ball supports from Example 3, the Fmoc protection group was removed by reacting 50 ml of Piperidine/DMF (1:1 v/v) with the ball supports for 10 minutes. Thus, an amine functionality from the Rink linker was liberated to act as the anchoring point for coupling the first diversity $R_1$ group building block to the linker substituted ball support by means of a covalent bond. The ball supports were then washed with DMF 6×50 ml, and split into two sets of four supports each, a first set to receive the $R_{1a}$ initial building block and a second set to receive the $R_{1b}$ initial building block. Alanine was selected as the $R_{1a}$ initial building block, accordingly Fmoc-Ala-OH (24 $\mu$mol, 3 equiv.), HOBt (24 $\mu$mol, 3 equiv.), and DIC (24 $\mu$mol, 3 equiv.), were dissolved in 10 ml DMF and charged into a glass reaction vessel containing the first set of four supports. Phenylalanine was selected as the $R_{1b}$ initial building block, accordingly Fmoc-Phe-OH (24 $\mu$mol, 3 equiv.), HOBt (24 $\mu$mol, 3 equiv.), and DIC (24 $\mu$mol, 3 equiv.), were dissolved in 10 ml DMF and charged into a glass reaction vessel containing the second set of four supports. The two diversity $R_1$ group building blocks $R_{1a}$ (Ala) and $R_{1b}$ (Phe) were allowed to react at 25° C. for 4 hours. The result was that the $R_1$ building block C-terminus carboxylic acid functionality formed an amide type covalent bond with the amine functionality of the Rink linker. In each case, when the reaction time ended, the supports were filtered from the reactant solution and washed with DMF 10×10 ml. The $R_1$ Fmoc N-terminus protecting group was subsequently removed by reacting 10 ml of Piperidine/DMF (1:1 v/v) for 10 minutes, resulting in the liberation of the amine moiety for covalent attachment of the diversity $R_2$ building block. The $R_1$ substituted ball supports were then washed with DMF 5×10 ml and DCM 5×10 ml. Finally the supports were dried under a vacuum for 1 hour.

EXAMPLE 5

Attachment of the Second Diversity $R_2$ Group Building Block to the R1 Substituted Ball Support Using the two sets of supports from Example 4 with $R_1$ building blocks in place, the first set of supports was loaded into a support transfer device and placed in four wells of a 96-deepwell filter plate equipped with a fritted filter bottom. The wells selected occurred in two rows (Rows A and B) with two wells in each row (Wells 1 and 2). Accordingly, the four wells were identified as wells A1, A2, B1, and B2. Next, the second set of supports was loaded into a support transfer device and placed in the same four wells on top of the first set of supports. Accordingly the supports in plane $Z_1$ on the bottom possessed the $R_{1a}$ building block Alanine, and the supports in plane $Z_2$ on the top possessed the $R_{1b}$ building block Phenylalanine. The diameter of the balls (³⁄₁₆ in) and the wells of the filter plate (¼ in) were sized such that the balls remained stacked in the desired order corresponding to their assigned locations in the 3D array during synthesis. A $R_{2a}$ solution of Fmoc-Ala-OH (24 $\mu$mol, 3 equiv.), HOBt (24 $\mu$mol, 3 equiv.), and DIC (24 $\mu$mol, 3 equiv.), was dissolved in 4 ml DMF and charged into Row A (wells A1 and A2) containing two stacked supports per well. Phenylalanine was selected as the $R_{2b}$ initial building block, accordingly Fmoc-Phe-OH (24 $\mu$mol, 3 equiv.), HOBt (24 $\mu$mol, 3 equiv.), and DIC (24 $\mu$mol, 3 equiv.), was dissolved in 4 ml DMF and charged into Row B (wells B1 and B2) containing two stacked supports per well. The two diversity $R_2$ group building blocks $R_{2a}$ (Ala) and $R_{2b}$ (Phe) were allowed to react at 25° C. for four hours. The result was that the $R_2$ building block C-terminus carboxylic acid formed an amide type covalent bond to the N-terminus amine functionality of the $R_1$ building block. In each case, when the reaction time ended, the supports were filtered from the reactant solution and washed with DMF 6×2 ml. The $R_2$ Fmoc protecting group was subsequently removed by reaction of 2 ml of Piperidine/DMF (1:1 v/v) per well for 10 minutes, resulting in the liberation of the N-terminus amine functionality for covalent attachment of the diversity $R_3$ building block. The ball supports were then washed with DMF 6×2 ml. Accordingly, the molecules thus far joined to the supports included:

| | Well Location |
|---|---|
| Plane $Z_1$ ($R_1$ = Ala) Compound | |
| H-Ala-Ala-Rink linker-PS-PP ball | A1 |
| H-Ala-Ala-Rink linker-PS-PP ball | A2 |
| H-Phe-Ala-Rink linker-PS-PP ball | B1 |
| H-Phe-Ala-Rink linker-PS-PP ball | B2 |
| Plane $Z_2$ ($R_1$ = Phe) Compound | |
| H-Ala-Phe-Rink linker-PS-PP ball | A1 |
| H-Ala-Phe-Rink linker-PS-PP ball | A2 |
| H-Phe-Phe-Rink linker-PS-PP ball | B1 |
| H-Phe-Phe-Rink linker-PS-PP ball | B2 |

EXAMPLE 6

Attachment of the Third Diversity $R_3$ Group Building Block to the $R_2$–$R_1$ Substituted Ball Support Completing 3D Diversity A $R_{3a}$ solution of Fmoc-Ala-OH (24 μmol, 3 equiv.), HOBt (24 μmol, 3 equiv.), and DIC (24 μmol, 3 equiv.), was dissolved in 4 ml DMF and charged into the first wells of each row (wells A1 and B1) containing two stacked supports per well. Phenylalanine was selected as the $R_{3b}$ initial building block, accordingly Fmoc-Phe-OH (24 μmol, 3 equiv.), HOBt (24 μmol, 3 equiv.), and DIC (24 μmol, 3 equiv.), were dissolved in 4 ml DMF and charged into the second wells of each row (wells A2 and B2) containing two stacked supports per well. The two diversity $R_3$ group building blocks $R_{3a}$ (Ala) and $R_{3b}$ (Phe) were allowed to react at 25° C. for four hours. The result was that the $R_3$ building block C-terminus carboxylic acid formed an amide type covalent bond to the N-terminus amine functionality of the $R_2$ building block. In each case, when the reaction time ended, the supports were filtered from the reactant solution and washed with DMF 6×2 ml. The $R_3$ Fmoc protecting group was subsequently removed by reaction 2 ml of Piperidine/DMF (1:1 v/v) per well for 10 minutes, resulting in the liberation of the N-terminus amine functionality. The ball supports were then washed with DMF 6×2 ml and DCM 6×2 ml. Finally, 3D diversity had been achieved by parallel synthesis of supports stacked in a 3D array. The supports were dried under vacuum to prepare for transfer of planes $Z_1$ (Ala) and $Z_2$ (Phe) into cleavage plates for cleavage of molecules from the supports. Accordingly, the molecules thus far joined to the supports included:

| | Well Location |
|---|---|
| Plane $Z_1$ ($R_1$ = Ala) Compound | |
| H-Ala-Ala-Ala-Rink linker-PS-PP ball | A1 |
| H-Phe-Ala-Ala-Rink linker-PS-PP ball | A2 |
| H-Ala-Phe-Ala-Rink linker-PS-PP ball | B1 |
| H-Phe-Phe-Ala-Rink linker-PS-PP ball | B2 |
| Plane $Z_2$ ($R_1$ = Phe) Compound | |
| H-Ala-Ala-Phe-Rink linker-PS-PP ball | A1 |
| H-Phe-Ala-Phe-Rink linker-PS-PP ball | A2 |
| H-Ala-Phe-Phe-Rink linker-PS-PP ball | B1 |
| H-Phe-Phe-Phe-Rink linker-PS-PP ball | B2 |

EXAMPLE 7

Distribution and Cleavage of Supports from a 3D Array to a 2D Array

Using the substituted ball supports in the filter plate from Example 6, the plane $Z_2$ ball supports were removed from the filter plate using a support transfer device and placed into a separate filter plate $P_2$ while maintaining the original filter plate array position of the supports in plane $Z_2$. This step was repeated for plane $Z_1$ ball supports and placed into a separate filter plate $P_1$ while maintaining the original filter plate array position of the supports in plane $Z_1$. A 0.5 aliquot of cleavage solution including TFA/H20 (19:1 v/v) was added to the four wells containing a support in each the two filter plates, and allowed to react at 25° C. for 2 hours. The cleavage solution was then removed by evaporation and the synthesized molecules were extracted from the wells by washing with methanol 2×0.5 ml and acetonitrile/$H_2$O (1:1 v/v) 1×0.5 ml. The solvent was extracted by filtration each time and collected in two new round bottom well type plates also defined correspondingly as plates $P_2$ and $P_1$. The solvents were evaporated from the extract and the resulting compounds were analyzed by HPLC, NMR, and mass spectroscopy for purity, structure, and mass information. From the supports in plates $P_2$ and $P_1$ the following structures were correctly identified:

| | Well Location |
|---|---|
| Plate $P_1$ Compound | |
| H-Ala-Ala-Ala-NH2 | A1 |
| H-Phe-Ala-Ala-NH2 | A2 |
| H-Ala-Phe-Ala-NH2 | B1 |
| H-Phe-Phe-Ala-NH2 | B2 |
| Plate $P_2$ Compound | |
| H-Ala-Ala-Phe-NH2 | A1 |
| H-Phe-Ala-Phe-NH2 | A2 |
| H-Ala-Phe-Phe-NH2 | B1 |
| H-Phe-Phe-Phe-NH2 | B2 |

EXAMPLE 8

Attachment of the Diversity $R_2$ Group Building Block to the R1 Substituted Ball Support Using the two sets of supports from Example 4 with $R_1$ building blocks in place, the first set of supports was loaded into a support transfer device and placed in four wells of a 96-deepwell filter plate equipped with a fritted filter bottom. The wells selected occurred in two rows (Rows A and B)

with two wells in each row (Wells 1 and 2). Accordingly, the four wells were identified as wells A1, A2, B1, and B2. Next, the second set of supports was loaded into a support transfer device and placed in the same four wells on top of the first set of supports. Accordingly the supports in plane $Z_1$ on the bottom possessed the $R_{1a}$ building block Alanine, and the supports in plane $Z_2$ on the top possessed the $R_{1b}$ building block Phenylalanine. The diameter of the balls (3/16 in) and the wells of the filter plate (1/4 in) were sized such that the balls remained stacked in the desired order corresponding to their assigned locations in the 3D array during synthesis. A $R_{2a}$ solution of 4-Hydroxybenzoic acid (24 μmol, 3 equiv.), HOBt (24 μmol, 3 equiv.), and DIC (24 μmol, 3 equiv.), were dissolved in 4 ml DMF and charged into Row A (wells A1 and A2) containing two stacked supports per well. Next, 3-Hydroxybenzoic acid was selected as the $R_{2b}$ initial building block, accordingly, 3-Hydroxybenzoic acid (24 μmol, 3 equiv.), HOBt (24 μmol, 3 equiv.), and DIC (24 μmol, 3 equiv.), were dissolved in 4 ml DMF and charged into Row B (wells B1 and B2) containing two stacked supports per well. The two diversity $R_2$ group building blocks $R_{2a}$ and $R_{2b}$ were allowed to react at 25° C. for 4 hours. The result was that the $R_2$ building block C-terminus carboxylic acid formed an amide type covalent bond to the N-terminus amine functionality of the $R_1$ building block. In each case, when the reaction time ended, the supports were filtered from the reactant solution, washed with DMF 6×2 ml, DCM 6×2 ml, and anhydrous THF 8×2 ml. Accordingly, the molecules thus far joined to the supports included:

|  | Well Location |
| --- | --- |
| Plane $Z_1$ ($R_1$ = Ala) Compound |  |
| 4-Hydroxybenzoic acid-Ala-Rink linker-PS-PP ball | A1 |
| 4-Hydroxybenzoic acid-Ala-Rink linker-PS-PP ball | A2 |
| 3-Hydroxybenzoic acid-Ala-Rink linker-PS-PP ball | B1 |
| 3-Hydroxybenzoic acid-Ala-Rink linker-PS-PP ball | B2 |
| Plane $Z_2$ ($R_2$ = Phe) Compound |  |
| 4-Hydroxybenzoic acid-Phe-Rink linker-PS-PP ball | A1 |
| 4-Hydroxybenzoic acid-Phe-Rink linker-PS-PP ball | A2 |
| 3-Hydroxybenzoic acid-Phe-Rink linker-PS-PP ball | B1 |
| 3-Hydroxybenzoic acid-Phe-Rink linker-PS-PP ball | B2 |

EXAMPLE 9

Attachment of the Third Diversity $R_3$ Group Building Block by Mitsunobu Reaction to the $R_2$–$R_1$ Substituted Ball Support Completing 3D Diversity A $R_{3a}$ solution of 4-(Hydroxymethyl)pyridine (72 μmol, 9 equiv.), Triphenylphosphine (72 μmol, 9 equiv.), and DIAD (72 μmol, 9 equiv.), were dissolved in 4 ml anhydrous THF and charged into the first wells of each row (wells A1 and B1) containing two stacked supports per well. Next, 2-(4-Nitrophenyl)ethanol was selected as the $R_{3b}$ initial building block, accordingly 2-(4-Nitrophenyl)ethanol (72 μmol, 9 equiv.), Triphenylphosphine (72 μmol, 9 equiv.), and DIAD (72 μmol, 9 equiv.), were dissolved in 4 ml anhydrous THF and charged into the second wells of each row (wells A2 and B2) containing two stacked supports per well. The two diversity $R_3$ group building blocks $R_{3a}$ and $R_{3b}$ were allowed to react at 25° C. for 15 hours. The result was that the $R_3$ alcohol building block formed an ether type covalent bond to the aromatic hydroxyl functionality of the $R_2$ building block. Finally, 3D diversity had been achieved by parallel synthesis of supports stacked in a 3D array. In each case, when the reaction time ended, the supports were filtered from the reactant solution, washed with THF 6×2 ml, DMF 6×2 ml, and DCM 6×2 ml. The supports were dried under vacuum in order to prepare for transfer of planes $Z_1$ (Ala), and $Z_2$ (Phe), into cleavage plates for cleavage of compound from the support.

EXAMPLE 10

Distribution and Cleavage of Supports from a 3D Array to a 2D Array

Using the ball supports in the filter plate from Example 9, the plane $Z_2$ ball supports were removed from the filter plate using a support transfer device and placed into a separate filter plate $P_2$ while maintaining the original filter plate array position of the supports in plane $Z_2$. This step was repeated for plane $Z_1$ ball supports and placed into a separate filter plate $P_1$ while maintaining the original filter plate array position of the supports in plane $Z_1$. A 0.5 ml aliquot of cleavage solution including TFA/H2O (19:1 v/v) was added to each of the four wells containing a support in the two filter plates, and allowed to react at 25° C. for 2 hours. The cleavage solution was then removed by evaporation and the synthesized molecules were extracted from the wells by washing with methanol 2×0.5 ml, and acetonitrile/H2O (1:1 v/v) 1×0.5 ml. The solvent was extracted by filtration each time and collected in two new round bottom well type plates. The solvents were evaporated from the extract and analyzed by HPLC, NMR, and mass spectroscopy for purity, structural information, and mass. From the supports in plates $P_2$ and $P_1$ the following structures were correctly identified:

Plate $P_1$ well A1

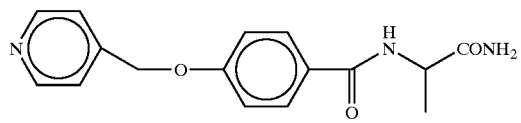

well A2

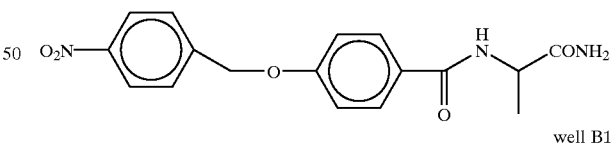

well B1

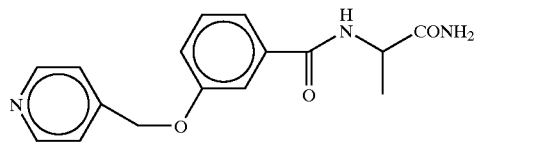

well B2

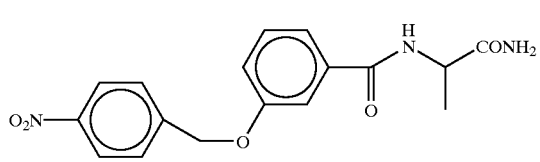

Plate P₂

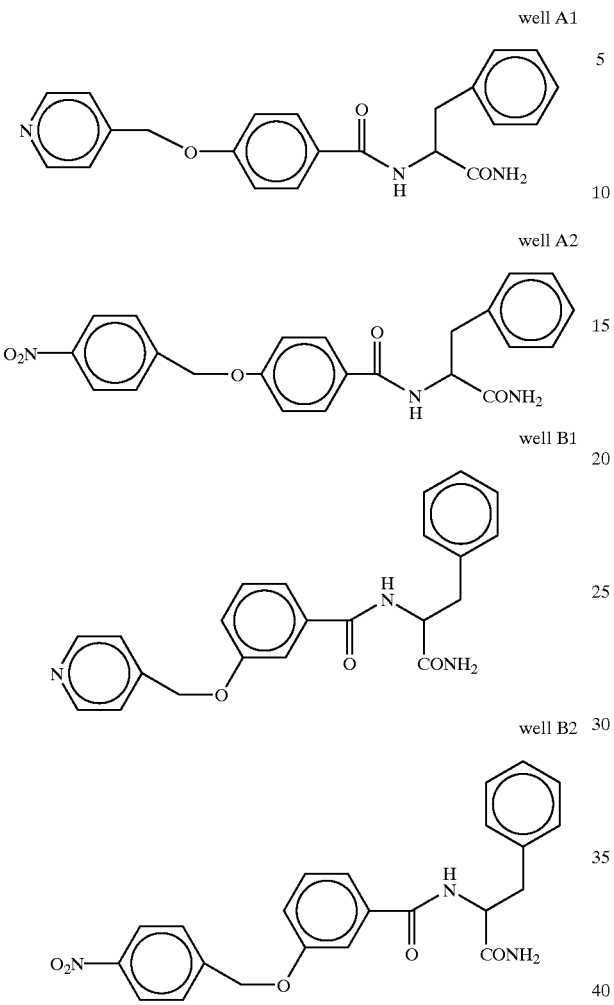

well A1 well A2 well B1 well B2

While the invention has been particularly shown and described with reference to preferred embodiments thereof, it will be understood by those skilled in the art that various changes in form and details may be made therein without departing from the spirit and scope of the invention. Accordingly, unless otherwise specified, any dimensions of the apparatus indicated in the drawings or herein are given as an example of possible dimensions and not as a limitation. Similarly, unless otherwise specified, any sequence of steps of the method indicated in the drawings or herein are given as an example of a possible sequence and not as a limitation.

What is claimed is:

1. An apparatus for performing parallel synthesis of a library of molecules with three-dimensional (3D) diversity, comprising:

a well plate comprising a plurality of wells in a two-dimensional (2D) array, each of said plurality of wells having one end which is open and one end which is closed; and a plurality of discrete solid phase supports disposed in each of said plurality of wells in a single stacked column arrangement, which arrangement forms a 3D array of solid phase supports for performing parallel synthesis of a library of molecules with 3D diversity, wherein said discrete supports are sized relative to said wells such that only a single stacked column arrangement of supports occupies each of said plurality of wells.

2. An apparatus for performing parallel synthesis of a library of molecules with 3D diversity, comprising:

a well plate comprising a plurality of parallel troughs in a two-dimensional (2D) array, each of said plurality of troughs having one end which is open and one end which is closed; and a plurality of discrete solid phase supports disposed in each of said plurality of troughs, which plurality of supports form a plurality of single stacked column arrangements, which arrangements forms a 3D array of solid phase supports for performing parallel synthesis of a library of molecules with 3D diversity, wherein said discrete solid phase supports are sized relative to said troughs such that a plurality of single stacked column arrangements of supports occupies each trough.

3. The apparatus as in claims 1 or 2, wherein the supports are functionalized.

4. The apparatus as in claims 1 or 2, wherein the supports are fabricated using material selected from the group consisting of resin, glass, silica gel, alumina gel, cellulose, polyolefins, polypropylene, polyethylene, polytetrafluoroethylene, poly(cholortrifluoroethylene), polyamides, polyimides, poly(paraxylylenes), and phenol-formaldehyde polymers, that are functionalized and compatible for use in combinatorial chemistry.

5. The apparatus as in claims 1 or 2, wherein individual locations in the 3D array are assigned to selected molecules in the library such that selected molecules are synthesized at and retrieved from their respective locations.

6. The apparatus as in claims 1 or 2, wherein the supports are selected from the group consisting essentially of rods, disks, tubes, rings, sheets, and spheres.

7. The apparatus as in claims 1 or 2, wherein the supports in said columns are coupled together.

8. The apparatus of claim 4, wherein the supports are fabricated using a halogenated polyolefin.

9. The apparatus of claim 3, wherein the supports comprise a functionalized graft co-polymer of polypropylene, polyethylene, polytetrafluoroethylene, poly (chlorotrifluoroethylene) or polyolefin.

10. The apparatus of claim 9, wherein the supports comprise a functionalized graft co-polymer of a halogenated polyolefin.

11. The apparatus as in claims 1 or 2, wherein the supports are rods.

12. The apparatus as in claims 1 or 2, wherein the supports are disks.

13. The apparatus as in claims 1 or 2, wherein the supports are tubes.

14. The apparatus as in claims 1 or 2, wherein the supports are rings.

15. The apparatus as in claims 1 or 2, wherein the supports are sheets.

16. The apparatus as in claims 1 or 2, wherein the supports are spheres.

17. The apparatus as in claims 1 or 2, wherein the supports are beads.

18. The apparatus of claims 1 or 2, wherein said supports comprise a releaseable coupling for interconnection of one of said supports to another.

19. The apparatus of claim 18, wherein said coupling mechanism comprises a plug on one of said supports and a complementary socket on an adjacent support.

20. The apparatus of claim 7, wherein said supports are disposed in a stackable enclosure, said enclosure being porous to allow for passage of reagent from one support to another within said column.

21. The apparatus of claim 20, wherein said stackable porous enclosure comprises a cup.

22. The apparatus of claim 20, wherein said supports are beads contained in said stackable porous enclosures, which enclosures are stacked in a column.

23. The apparatus of claims 1 or 2, wherein said supports are stacked tubes having axially aligned apertures with a rod passing through the apertures of the tubes of a stack.

* * * * *

UNITED STATES PATENT AND TRADEMARK OFFICE
CERTIFICATE OF CORRECTION

PATENT NO. : 6,872,535 B2
DATED : March 29, 2005
INVENTOR(S) : Stephen A. Baum

It is certified that error appears in the above-identified patent and that said Letters Patent is hereby corrected as shown below:

<u>Column 30,</u>
Line 27, the term "poly(cholortrifluoroethylene)" should read -- poly(chlorotrifluoroethylene) --.

Signed and Sealed this

Twenty-sixth Day of July, 2005

JON W. DUDAS
*Director of the United States Patent and Trademark Office*